(12) United States Patent
Thienphrapa et al.

(10) Patent No.: US 11,937,883 B2
(45) Date of Patent: Mar. 26, 2024

(54) GUIDED ANATOMICAL VISUALIZATION FOR ENDOSCOPIC PROCEDURES

(71) Applicant: KONINKLIJKE PHILIPS N.V., Eindhoven (NL)

(72) Inventors: Paul Thienphrapa, Cambridge, MA (US); Torre Michelle Bydlon, Melrose, MA (US); Prasad Vagdargi, Cambridge, MA (US); Sean Joseph Kyne, Brookline, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 143 days.

(21) Appl. No.: 17/115,850

(22) Filed: Dec. 9, 2020

(65) Prior Publication Data
US 2021/0177524 A1 Jun. 17, 2021

Related U.S. Application Data

(60) Provisional application No. 62/947,145, filed on Dec. 12, 2019.

(51) Int. Cl.
*A61B 34/20* (2016.01)
*A61B 1/00* (2006.01)

(52) U.S. Cl.
CPC .......... *A61B 34/20* (2016.02); *A61B 1/00006* (2013.01); *A61B 1/00045* (2013.01); *A61B 2034/2055* (2016.02)

(58) Field of Classification Search
CPC . A61B 34/20; A61B 1/00006; A61B 1/00045; A61B 2034/2055
See application file for complete search history.

(56) References Cited

U.S. PATENT DOCUMENTS

6,346,940 B1* 2/2002 Fukunaga ............... G06T 15/20 382/103
2016/0183841 A1* 6/2016 Duindam ............... A61B 5/743 600/424

(Continued)

FOREIGN PATENT DOCUMENTS

WO 2017044965 A1 3/2017

OTHER PUBLICATIONS

Ko et al: "Intelligent Interaction Between Surgeon and Laparoscopic Assistant Robot System"; 2005 IEEE International Workshop On Robots and Human Interactive Communication, pp. 60-65.

*Primary Examiner* — Rochelle D Turchen

(57) ABSTRACT

Various embodiments of the present disclosure encompass a visual endoscopic guidance device employing an endoscopic viewing controller (20) for controlling a display of an endoscopic view (11) of an anatomical structure, and a visual guidance controller (130) for controlling a display one or more guided manipulation anchors (50-52) within the display of the endoscopic view (11) of the anatomical structure. A guided manipulation anchor (50-52) is representative of location marking and/or a motion directive of a guided manipulation of the anatomical structure. The visual guidance controller (130) further controls a display of a hidden feature anchor relative to the display of the endoscopic view (11) of the anatomical structure. The hidden feature anchor (53) being representative of a position (e.g., a location and/or an orientation) of a guided visualization of the hidden feature of the anatomical structure.

18 Claims, 17 Drawing Sheets

(56) References Cited

U.S. PATENT DOCUMENTS

| | | |
|---|---|---|
| 2017/0252095 A1 | 9/2017 | Johnson |
| 2019/0175062 A1* | 6/2019 | Rafii-Tari ............... A61B 34/20 |

* cited by examiner

GUIDED ANATOMICAL VISUALIZATION FOR ENDOSCOPIC PROCEDURES

FIELD OF THE INVENTION

The present disclosure generally relates to image guided endoscopic based diagnostic procedures, therapeutic procedures and surgical procedures. The present disclosure specifically relates to a guided visualization of a hidden feature of an anatomical structure within/relative to an endoscopic view of the anatomical structure.

BACKGROUND OF THE INVENTION

In minimally invasive surgery, a surgeon views the tissue under treatment using a camera that extends into the patient's body. These cameras are called endoscopes and a particular type of endoscope being utilized is dependent on the procedure being performed (e.g., anoscopy, arthroscopy, bronchoscopy, colonoscopy, colposcopy, cystoscopy, esophagoscopy, gastroscopy, laparoscopy, laryngoscopy, neuroendoscopy, proctoscopy, sigmoidoscopy and thoracoscopy).

During the surgery, the surgeon performs visual inspection and exploration of the subject anatomical region via an endoscope prior to the primary surgical tasks to thereby gain familiarity with the patient's anatomy and identify important anatomical structures (e.g., known blood vessels and nerves). In doing so, the surgeon familiarizes themselves with the patient's tissue, which the surgeon had not seen hitherto. Endoscopy has traditionally been used in this manner as a passive visualization tool.

Depending on the procedure, the surgeon may attempt to relate what he/she has seen with what they know from preoperative information, including anatomical imaging as well as experience and textbook anatomical knowledge. However, tissue seen under the endoscopic view is often not immediately recognizable by the surgeon, because the field of view is limited to a small area that is difficult to contextualize in isolation. While preoperative planning may be used to determine the best course of surgical action, as the intervention begins, there may not be enough information revealed to fully combine the preoperative information to endoscopy. Then as the intervention proceeds, any information fusion already obtained may be rendered invalid by tissue deformation, physiological motion, patient motion, and so on. For the intervention to reference a plan, endoscope views must be continuously analyzed and updated to evolving surgical conditions.

More particularly, a visual appearance of a particular patient's anatomy is unknown until surgery time, because preoperative information via scans (e.g., X-ray, computed-tomography (CT), positron-emission tomography (PET), etc.) primarily show differences in attenuation of tissue to radiation energy, which delineate structures such as tumors, vessels, and airways. A preliminary activity in minimally invasive endoscopic surgery is thus gaining familiarity with the tissue appearance. During this exploratory phase, the surgeon views tissue through the endoscope while performing manipulations using tools, and simultaneously dissecting tissue to expose anatomical structures while identifying landmarks to facilitate the primary surgical task. For example, in tumor resection, the surgeon attempts to identify blood vessels and other structures in the proximity of the tumor, in order to avoid damaging them during resection.

This exploration phase is a time consuming, uncertain, and unquantifiable activity that makes many aspects of surgical procedures difficult to reproduce. An existing approach fuses preoperative information (e.g., an X-ray scan, a CT scan, a PET scan, etc.) into the endoscopic view. In practice, however, the image fusion approach largely fails due to extreme tissue deformation, difficult depth visualization, and artifacts of imaging (e.g., specularities, occlusions, shadows, small field of view, motion blur, and focus blur).

Furthermore, revealing of an anatomical feature of interest within an image is important to a clinician, but typically such anatomical feature of interest is not present within an endoscopic view of the anatomy structure. There are various reasons for failure to visualize an anatomical feature of interest within an image, such as, for example, the anatomical feature of interest being outside of the endoscopic field of view or the anatomical feature of interest being obscured by other tissue, blood, smoke, instruments, etc. Moreover, the anatomical structure may be deformed beyond recognition. These difficulties are exacerbated by the relatively limited field of view provided by endoscopes, coupled with the dynamically deforming nature of surgical tissue in which anatomical relations are not instantly recognizable. These issues challenge clinicians' sense of context and demand significant cognitive effort and physical exploration to overcome.

SUMMARY OF THE INVENTION

The present disclosure describes a novel, unique controller generation of preferred guided manipulations of an anatomical structure (e.g., tissue, bone, nerves and blood vessels) and guided visualization of a hidden feature of the anatomical structure that are communicated to a clinician (e.g., a radiologist, a therapist or a surgeon) during an endoscopic procedure. Examples of such guided manipulations include, but are not limited to, a grasping, a pulling, a pushing, a sliding, a reorienting, a tilting, a dissecting, a bending, a twisting, a flexing, an extending, a compressing, a removing and/or a repositioning of an anatomical structure during an endoscopic based diagnostic procedure, an endoscopic based therapeutic procedure and/or an endoscopic based surgical procedure. The clinician may manually or robotically implement the guided manipulation, or a controller may automatically control robotic instruments to manipulate the tissue based on the guided visualization of the hidden feature of the anatomical structure to thereby facilitate a partial or a full exposure of the hidden feature within a field of view of the endoscope.

The present disclosure may be embodied as (1) a visual guidance controller, (2) a visual endoscopic guidance device incorporating the manipulative guidance controller, (3) a visual endoscopic guidance system incorporating the manipulative endoscopic guidance device, (4) a visual endoscopic guidance method utilizing the manipulative guidance controller, (5) a visual endoscopic guidance method utilizing the manipulative endoscopic guidance device and (6) a visual endoscopic guidance method utilizing the visual endoscopic guidance system.

Various visual guidance controller embodiments of the present disclosure encompass a visual guidance controller for controlling a display of one or more guided manipulation anchors within a display of an endoscopic view of an anatomical structure, and for controlling a display of a hidden feature anchor relative to the display of the endoscopic view of the anatomical structure.

A guided manipulation anchor is representative of a location marking and/or a motion directive of a guided manipulation of the anatomical structure relative to a hidden feature of the anatomical structure including, but not limited to, a grasping, a pulling, a pushing, a sliding, a reorienting, a tilting, a removing, and/or a repositioning of the anatomical structure during an endoscopic based diagnostic procedure, an endoscopic based therapeutic procedure and/or an endoscopic based surgical procedure in pursuit of partially or fully exposing the hidden feature within a field of view of the endoscope.

For purposing of claiming and describing the present disclosure, the phrase "a guided manipulation of the anatomical structure relative to a hidden feature of the anatomical structure" encompasses the hidden feature of the anatomical structure serving as a reference for deriving a guided manipulation of the anatomical structure to partially or fully expose the hidden feature within a field of view of the endoscope.

The hidden feature anchor is representative of a position (e.g., a location and/or an orientation) of a guided visualization of the hidden feature of the anatomical structure including, but not limited to, an anchor informative of a position of the hidden feature of the anatomical structure relative to an endoscopic view of the anatomical structure or relative to an image map including the endoscopic view of the anatomical structure.

For purposing of claiming and describing the present disclosure, the phrase "the hidden feature anchor relative to the display of the endoscopic view of the anatomical structure" encompasses the endoscopic view of the anatomical structure serving as a reference for deriving a guided visualization of the hidden feature of the anatomical structure including, but not limited to, a configuration of an overlay informative of a two-dimensional or a three-dimensional directional vector from the pose of the endoscopic view of the anatomical structure to the position of the hidden feature within the anatomical structure.

A clinician (e.g., a radiologist, a therapist or a surgeon) may manually or robotically implement the guided manipulation as displayed, or the manipulative guidance controller may automatically control robotic instruments to manipulate the tissue accordingly.

The visual guidance controller may generate a guided manipulation anchor (1) by analyzing a correlation of the endoscopic view of the anatomical structure with a knowledge base of image(s), model(s) and/or detail(s) corresponding to the anatomical structure; (2) by identifying a position (i.e., location and/or orientation) of the hidden feature within the image(s) and/or the model(s) of anatomical structure as detailed in the knowledge base; and (3) by deriving the guided manipulation anchor based on a degree of correlation of the endoscopic view of the anatomical structure with the image(s) and/or the model(s) of anatomical structure as detailed in the knowledge base and a degree of confidence of a determined spatial pose of the endoscopic view of the anatomical structure relative to the position of the hidden feature within the anatomical structure.

The visual guidance controller may generate a hidden feature anchor by deriving the hidden feature anchor based on a degree of confidence in the identification of the position of the hidden anatomical feature the image(s) and/or the model(s) of anatomical structure as correlated to the endoscopic view of the anatomical structure.

The visual guidance controller may receive the endoscopic view of the anatomical structure or may ascertain the endoscopic view of the anatomical structure from a tracked positioning of an endoscope relative to a partial or whole volume scan of an anatomical structure.

Various visual endoscopic guidance device embodiments encompass the visual guidance controller and an endoscopic viewing controller for controlling the display of the endoscopic view of the anatomical structure. Examples of an endoscopic viewing controller include, but are not limited to, controllers for implementing endoscopic based diagnostic, therapeutic and/or surgical guidance of tools and instruments within an anatomical region as known in the art of the present disclosure and hereinafter conceived.

Various visual endoscopic guidance system embodiments encompass the visual endoscopic guidance device and an endoscope as known in the art of the present disclosure and hereinafter conceived for generating the endoscopic view of the anatomical structure. Examples of the endoscope include, but are not limited to, an anoscope, an arthroscope, a bronchoscope, a colonoscope, a colposcope, a cystoscope, an esophagoscope, a gastroscope, a laparoscope, a laryngoscope, a neuroendoscope, a proctoscope, a sigmoidoscope and a thoracoscope.

Various visual endoscopic guidance method embodiments of the present disclosure encompass the visual guidance controller controlling a display of one or more manipulation anchors within a display of the endoscopic view of the anatomical structure and controlling a display of a hidden feature anchor relative to the display of the endoscopic view of the anatomical structure. As previously set forth, (1) the guided manipulation anchor is representative of a location marking and/or a motion directive of a guided manipulation of the anatomical structure relative to a hidden feature of the anatomical structure including, but not limited to, a grasping, a pulling, a pushing, a sliding, a reorienting, a tilting, a removing, and/or a repositioning of the anatomical structure during an endoscopic based diagnostic procedure, an endoscopic based therapeutic procedure and/or an endoscopic based surgical procedure in pursuit of partially or fully exposing the hidden feature within a field of view of the endoscope, and (2) the hidden feature anchor is representative of a position (e.g., a location and/or an orientation) of a guided visualization of the hidden feature of the anatomical structure including, but not limited to, an informative overlay of the position of the hidden feature of the anatomical structure within an endoscopic view of the anatomical structure or within an image map including the endoscopic view of the anatomical structure.

A clinician (e.g., a radiologist, a therapist or a surgeon) may manually or robotically implement the guided manipulation as displayed, or the visual guidance controller may automatically control robotic instruments to manipulate the tissue accordingly.

The method may involve the visual guidance controller generating a guided manipulation anchor (1) by analyzing a correlation of the endoscopic view of the anatomical structure with a knowledge base of image(s), model(s) and/or detail(s) corresponding to the anatomical structure; (2) by identifying a position (i.e., location and/or orientation) of the hidden feature within the anatomical structure; and (3) by deriving the guided manipulation anchor based on a degree of correlation of the endoscopic view of the anatomical structure with the knowledge base and a degree of confidence of a determined spatial pose of the endoscopic view of the anatomical structure relative to the position of the hidden feature within the anatomical structure.

The visual guidance controller may receive the endoscopic view of the anatomical structure or may ascertain the endoscopic view of the anatomical structure from a tracked positioning of an endoscope relative to a partial or whole volume scan of an anatomical structure.

The visual endoscopic guidance method may further involve an endoscope generating the endoscopic view of the anatomical structure and/or an endoscopic viewing controller controlling the display of the endoscopic view of the anatomical structure.

The foregoing embodiments and other embodiments of the present disclosure as well as various structures and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

BRIEF DESCRIPTION OF THE DRAWINGS

The present disclosure will present in detail the following description of exemplary embodiments with reference to the following figures wherein.

DETAILED DESCRIPTION OF THE PREFERRED EMBODIMENTS

Figure 1:
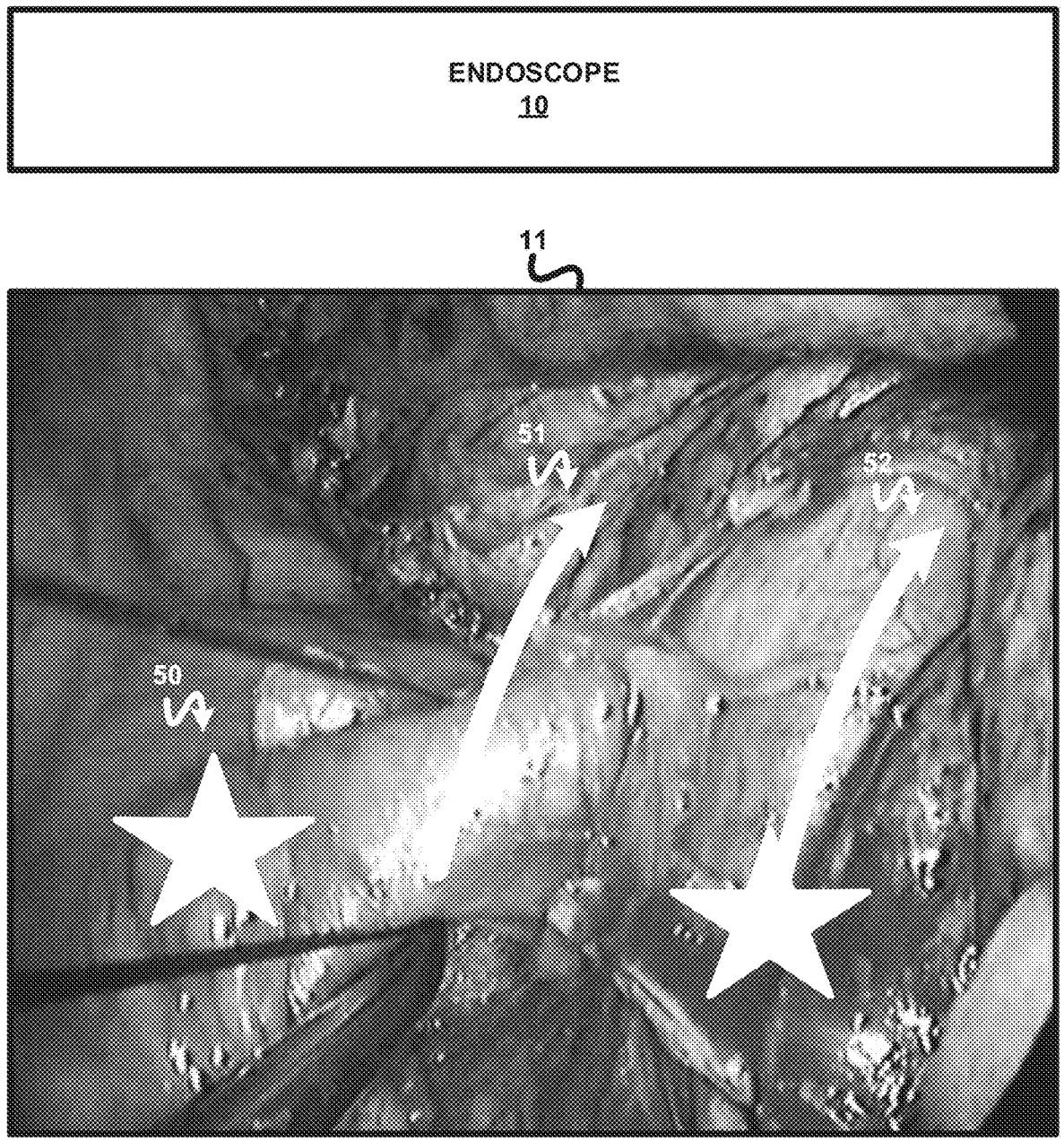
FIG. 1 illustrates an exemplary embodiment of a manipulative endoscopic guidance device in accordance with the present disclosure.

The present disclosure is applicable to numerous and various diagnostic, therapeutic and surgical procedures utilizing an endoscope including, but not limited to, anoscopy, arthroscopy, bronchoscopy, colonoscopy, colposcopy, cystoscopy, esophagoscopy, gastroscopy, laparoscopy, laryngoscopy, neuroendoscopy, proctoscopy, sigmoidoscopy and thoracoscopy.

The present disclosure improves upon the prior art of endoscopic procedures by providing guided manipulations for a clinician (e.g., a radiologist, a therapist or a surgeon) on how to manually or robotically manipulate anatomical structure(s) (e.g., tissue, bone, nerves and blood vessels) in an endoscopic view of the anatomical structure(s) that may (1) reveal hidden anatomical structure(s) within the endoscopic view and/or (2) reposition and/or reorient anatomical structures(s) within the endoscopic view to facilitate a diagnostic analysis, a therapeutic treatment and/or a surgical operation of the anatomical structure(s) within the endoscopic view.

For purposes of describing and claiming the present disclosure, the term "guided manipulation" broadly encompasses, as known in the art of the present disclosure and hereinafter conceived, a delineated contact of a tool/instrument with an anatomical structure for purposes of altering, reshaping, distorting, transforming or otherwise manipulating a configuration, a position and/or an orientation of the anatomical structure within an endoscopic view of the anatomical structure.

Examples of guided manipulations include, but are not limited to, a grasping, a pulling, a pushing, a sliding, a tilting, a dissecting, a bending, a twisting, a flexing, an extending, a compressing and/or removing of an anatomical structure during an endoscopic procedure.

One objective of the guided manipulation may be a manipulation of an anatomical structure within the endoscopic view into a more known, baseline, or recognizable state to the clinician for facilitating a diagnostic analysis, a therapeutic treatment and/or a surgical operation of the anatomical structure.

Another objective of a guided manipulation may be an exposure of additional anatomical structure(s) hidden within the endoscopic view for facilitating a diagnostic analysis, a therapeutic treatment and/or a surgical operation of the additional anatomical structure(s) within the endoscopic view.

Additionally there are a variety of uses of a guided manipulation of the present disclosure. Examples of such uses include, but are not limited to, (1) an exposure of oblique facing tissue to the endoscope to facilitate a better understanding of the endoscopic view, (2) a combining of endoscopic views to stitch larger pictures of a corresponding anatomical region (e.g., a thorax region, an abdomen region, etc.), (3) an ability to restore views that are no longer within a field of view of the endoscope or that have been hidden behind other objects, and (4) a use of force sensing to apply known amounts of force to anatomical structure(s).

For purposes of describing and claiming the present disclosure, the term "anchor" broadly encompasses a visual representation, as known in the art of the present disclosure and hereinafter conceived, for continually marking a specific location within view of an imaging modality, and the term "guided manipulation anchor" broadly encompasses a visual representation, in accordance with the present disclosure, of a location marking and/or a motion directive of a guided manipulation within an endoscopic view of an anatomical structure whereby a clinician (e.g., a radiologist, a therapist or a surgeon) may manually or robotically implement the guided manipulation of the anatomical structure(s), or a controller may automatically control robotic instruments to manipulate the anatomical structure(s) accordingly.

In practice, a guided manipulation anchor of the present disclosure may be overlaid on an endoscopic video feed whereby the anchor is a static visual augmentation on any type of physical, virtual or augmented display (e.g., display monitors, head mounted displays, etc.). Additionally, the display may render a 3D model of the scene if such data is available. A guided manipulation anchor of the present disclosure may also be dynamic whereby the guided manipulation anchor appears to adhere to the associated anatomical structure (e.g., tissue, bone, nerves and blood vessels).

For example, if a grasp location is on the outer edge of an organ, the anchor overlay that tells a surgeon to grasp there may track with the underlying tissue as it moves. Consequently, the anchor overlay may disappear if the tissue goes out of the view or becomes hidden, and reappear with the connected tissue. Guided manipulation anchor may be put on tools/instruments as well to communicate how tools/instruments should be moved.

Further in practice, visually, a guided manipulation anchor of the present disclosure may be opaque to grab the clinician's attention, or translucent to allow vison by the clinician to the anatomical structure(s) behind the guided manipulation anchor. Guided manipulation anchors of the present disclosure may also vary by the nature of the anchors (e.g., informative or query within a context of the diagnostic, therapeutic and/or surgical endoscopic procedure). The shapes, colors, and sizes of a guided manipulation anchors of the present disclosure may be similarly adjusted to communicate messages. For examples, a shape of a guided manipulation anchor of the present disclosure may be oriented to communicate a directionality of anatomical manipulation and/or may be animated to show motion suggestions.

Also in practice, guided manipulation anchors of the present disclosure may be communicated through means beyond visualization. For example, a haptic display maybe shaped or colored or a haptic joystick may be vibrated to communicate to the clinician that the instrument location is at a grasp point near tissue. Other nonlimiting communication means include audible cues and combinations of haptic stimuli.

Additionally in practice, directionality of anatomical manipulation may be determined based on a combination of how the anatomical structure is oriented in the endoscopic view and the immediate task(s) to be performed during the endoscopic procedure. For example, if tissue to be grasped is an edge of an organ, then a direction should be into the organ for a folding motion and outward for a stretching motion. An embodiment of determining tissue characteristics may involve torsion motion of the tissue grasp as well to thereby allow for an execution of a desired motion in a preferred direction of tissue.

More particularly, a direction of anatomical manipulation may be computed based on efficient task execution and workflow as well. For example, if it is known that a particular incision is most safely and efficiently performed at a certain angle, then a clinician may be guided on staging the tissue to that angle. Also a direction of anatomical manipulation may be computed based on intraoperative criteria such as, for example, current angulation of tissue, camera, and instruments, which also may be extended to one or more sequences of tasks.

Figure 2A:
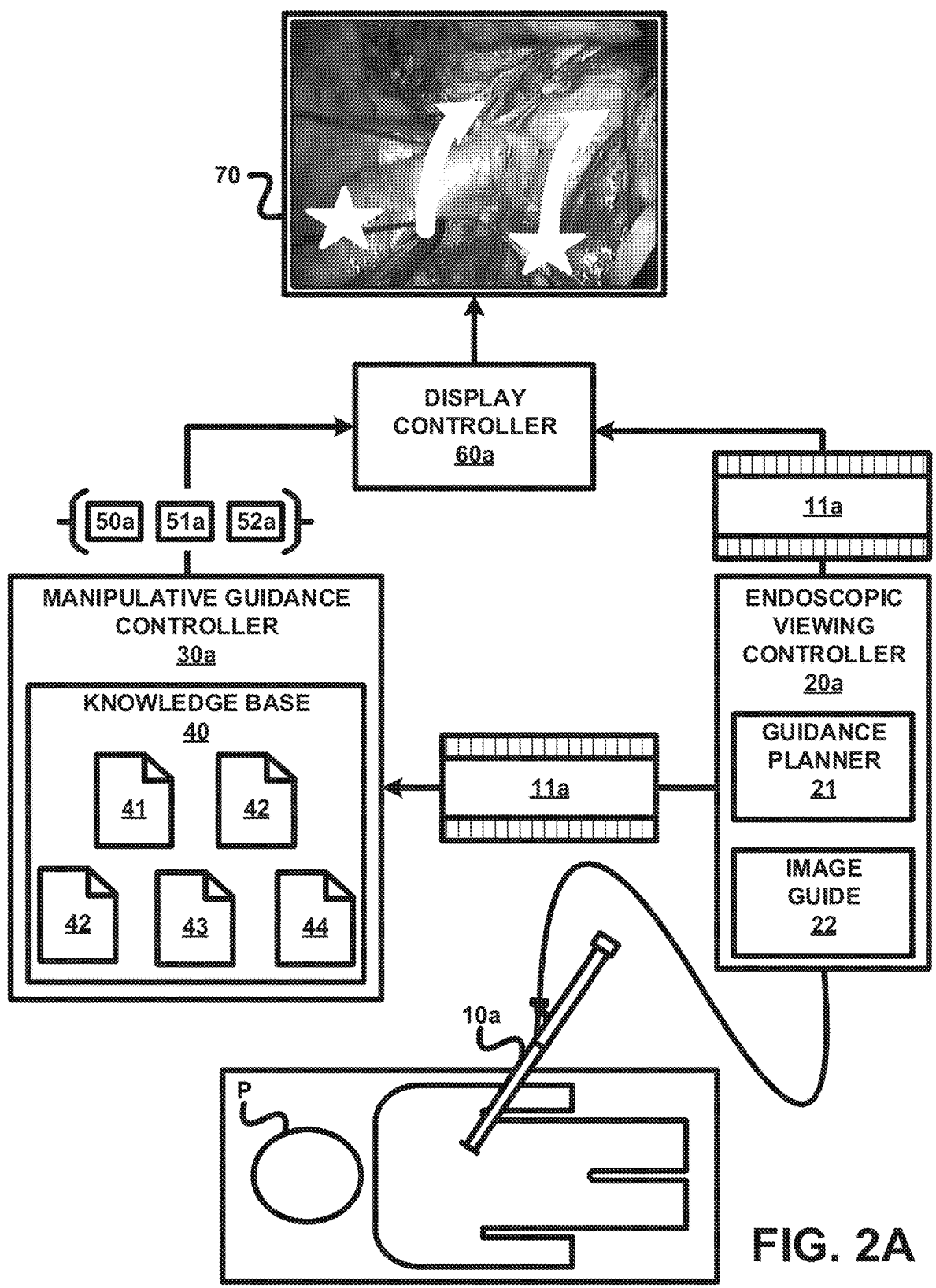
FIGS. 2A-2C illustrate exemplary embodiments of the manipulative endoscopic guidance device of FIG. 1 in accordance with the present disclosure.
Figure 2B:
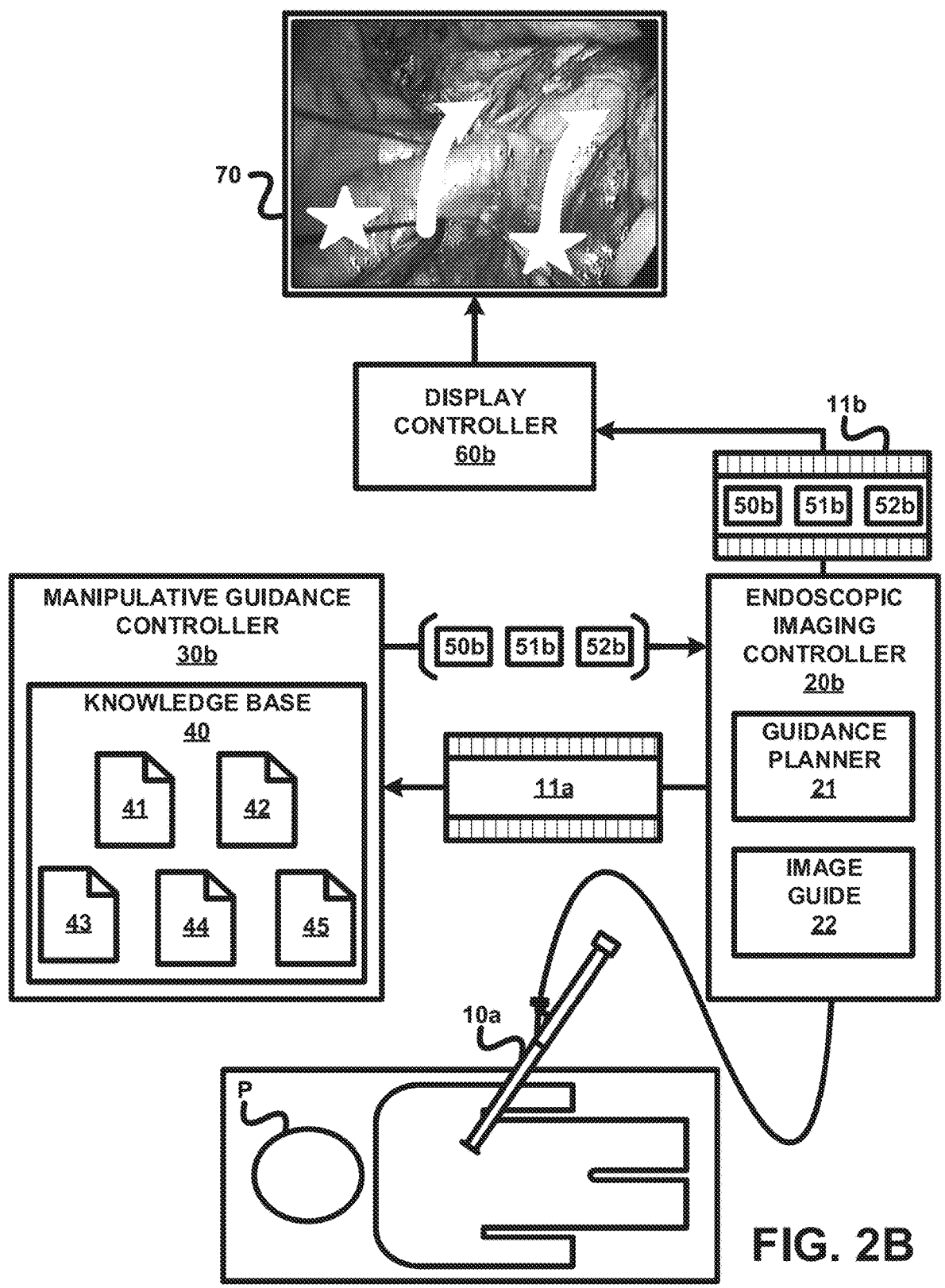
Figure 2C:
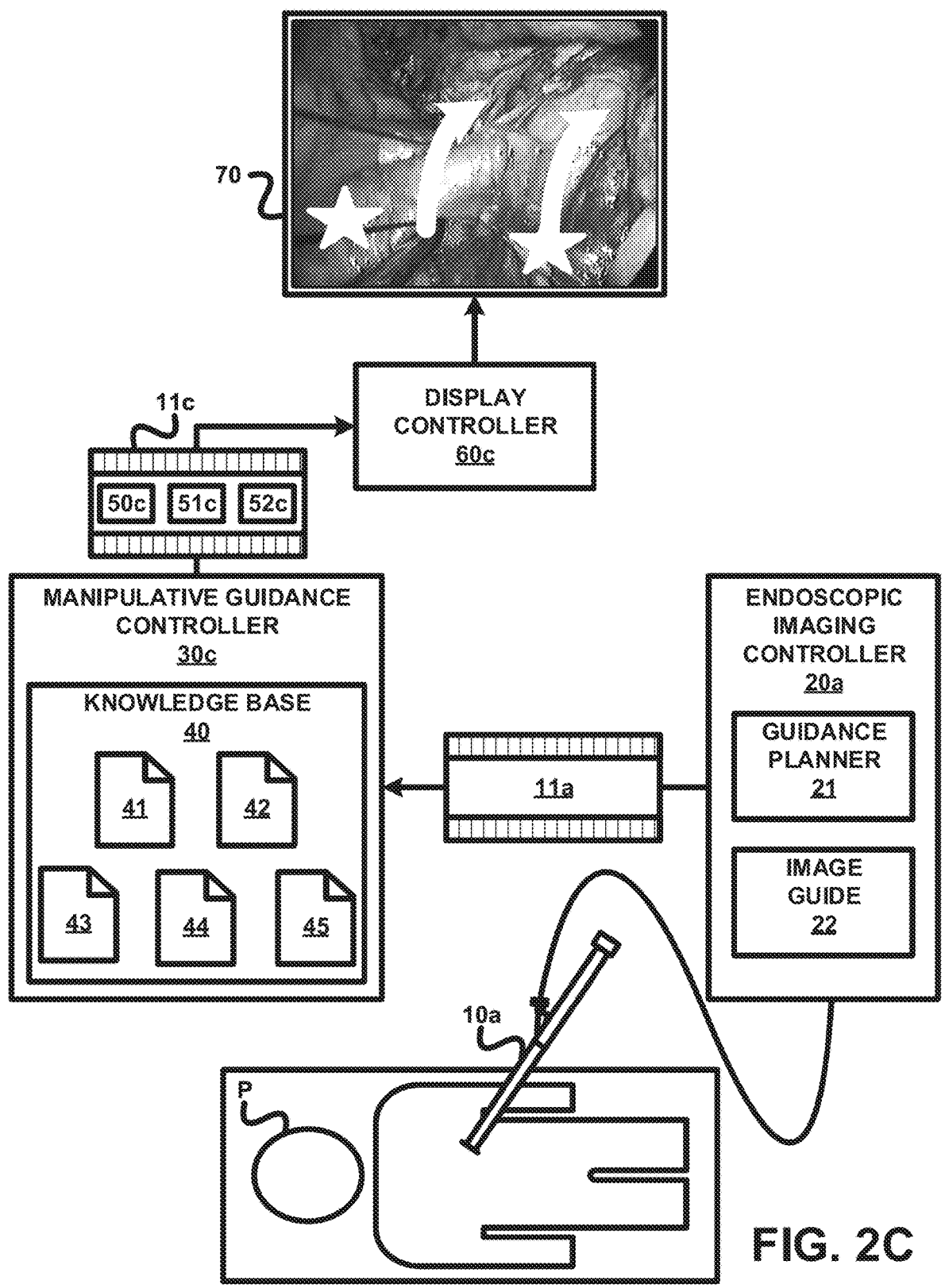

To facilitate an understanding of a guided manipulation of the present disclosure, the following description of FIGS. 1-2C teaches respective exemplary embodiments of a manipulative endoscopic guidance device in accordance with the present disclosure. From the description of FIGS. 1-2C, those having ordinary skill in the art of the present disclosure will appreciate how to apply the present disclosure to make and use additional embodiments of manipulative endoscopic guidance devices in accordance with the present disclosure.

Referring to FIG. 1, an endoscope 10 is an endoscope as known in the art of the present disclosure or hereinafter conceived for generating an endoscopic view of the anatomical structure, such as, for example, an endoscopic view 11 of a lung as shown in FIG. 1. Examples of the endoscope include, but are not limited to, an anoscope, an arthroscope, a bronchoscope, a colonoscope, a colposcope, a cystoscope, an esophagoscope, a gastroscope, a laparoscope, a laryngoscope, a neuroendoscope, a proctoscope, a sigmoidoscope and a thoracoscope.

The present disclosure provides a manipulative endoscopic guidance device employing an endoscopic viewing controller 20 and a manipulate guidance controller 30.

For purposes of describing and claiming the present disclosure, the term "endoscopic viewing controller" encompasses all structural configurations, as understood in the art of the present disclosure and as exemplary described in the present disclosure, of a main circuit board or an integrated circuit for controlling an application of various principles of the present disclosure for controlling a display of the endoscopic view of an anatomical structure as known in the art of present disclosure or hereinafter conceived. The structural configuration of the endoscopic viewing controller may include, but is not limited to, processor(s), computer-usable/computer readable storage medium(s), an operating system, application module(s), peripheral device controller (s), slot(s) and port(s).

For purposes of describing and claiming the present disclosure, the term "application module" as related to an endoscopic viewing controller broadly encompasses an application incorporated within or accessible by an endoscopic viewing controller consisting of an electronic circuit (e.g., electronic components and/or hardware) and/or an executable program (e.g., executable software stored on non-transitory computer readable medium(s) and/or firmware) for executing a specific application associated for controlling a display of the endoscopic view of an anatomical structure as known in the art of present disclosure or hereinafter conceived.

Examples of an endoscopic viewing controller 20 include, but are not limited to, endoscopic viewing controllers for implementing endoscopic based diagnostic, therapeutic and/or surgical guidance of tools and instruments within an anatomical region as known in the art of the present disclosure and hereinafter conceived.

Still referring to FIG. 1, for purposes of describing and claiming the present disclosure, the term "manipulative guidance controller" encompasses all structural configurations, as understood in the art of the present disclosure and as exemplary described in the present disclosure, of a main circuit board or an integrated circuit for applying various principles of the present disclosure for controlling a display of one or more guided manipulation anchors within a display of an endoscopic view of an anatomical structure in accordance with the present disclosure. The structural configuration of the manipulative guidance controller may include, but is not limited to, processor(s), computer-usable/computer readable storage medium(s), an operating system, application module(s), peripheral device controller(s), slot(s) and port(s).

For purposes of describing and claiming the present disclosure, the term "application module" as related to a manipulative guidance controller broadly encompasses an application incorporated within or accessible by a manipulative guidance controller consisting of an electronic circuit (e.g., electronic components and/or hardware) and/or an executable program (e.g., executable software stored on non-transitory computer readable medium(s) and/or firmware) for executing a specific application associated controlling a display of one or more guided manipulation anchors within a display of an endoscopic view of an anatomical structure in accordance with the present disclosure.

As previously described herein, a guided manipulation anchor is representative of a location marking and/or a motion directive of a guided manipulation of the anatomical structure including, but not limited to, a grasping, a pulling, a pushing, a sliding, a reorienting, a tilting, a removing, and/or a repositioning of the anatomical structure during an endoscopic based diagnostic procedure, an endoscopic based therapeutic procedure and/or an endoscopic based surgical procedure. A clinician (e.g., a radiologist, a therapist or a surgeon) may manually or robotically implement the guided manipulation as displayed, or the manipulative guidance controller may automatically control robotic instruments to manipulate the tissue accordingly.

For example, a guided manipulation anchor 50 as overlaid on endoscopic view 11 of a lung is representative of a location marking of a guided manipulation of the anatomical structure whereby a shape, a color and/or a size of guided manipulation anchor 50 may expressly communicate a particular type of guided manipulation of the anatomical structure (e.g., a grasping, a pulling, a pushing, a sliding, a reorienting, a tilting, a removing, and/or a repositioning of the anatomical structure).

By further example, a guided manipulation anchor 51 as overlaid on endoscopic view 11 of a lung is representative of a motion directive of a guided manipulation of the anatomical structure whereby a shape, a color and/or a size of guided manipulation anchor 50 may expressly communicate a particular type of guided manipulation of the anatomical structure (e.g., a grasping, a pulling, a pushing, a sliding, a reorienting, a tilting, a removing, and/or a repositioning of the anatomical structure).

By further example, a guided manipulation anchor 52 as overlaid on endoscopic view 11 of a lung is representative of a location marking and a motion directive of a guided manipulation of the anatomical structure whereby a shape, a color and/or a size of guided manipulation anchor 50 may expressly communicate a particular type of guided manipulation of the anatomical structure (e.g., a grasping, a pulling, a pushing, a sliding, a reorienting, a tilting, a removing, and/or a repositioning of the anatomical structure).

Still referring to FIG. 1, in practice, manipulative guidance controller 30 generates a guided manipulation anchor in dependence of the endoscopic view of the anatomical structure in a context of the endoscopic based diagnostic procedure, an endoscopic based therapeutic procedure and/or an endoscopic based surgical procedure.

In one embodiment as will be further described in the present disclosure, manipulative guidance controller 30 may generate a guided manipulation anchor (1) by analyzing a correlation of the endoscopic view of the anatomical structure with a knowledge base of image(s), model(s) and/or detail(s) corresponding to an anatomical structure and (2) by deriving the guided manipulation anchor based on a degree of correlation of the endoscopic view of the anatomical structure with the knowledge base.

For purposes of describing and claims the present disclosure, the term "correlation" broadly encompasses an endoscopic view having a mutual relationship with a target view of an anatomical structure. Examples of a mutual relationship includes, but is not limited to, (1) an image matching of the endoscopic view to the target view within a volume scan of the anatomical structure, (2) an imaging matching of the endoscopic view to a target view on a model of the anatomical structure, (3) an imaging matching of the endoscopic view to a target view of an image compilation of anatomical structure, (4) an imaging matching of anatomical features illustrated within the endoscopic view to with salient anatomical features illustrated within the target view, and (5) an evolving image matching of the endoscopic view to the target view as treatment tasks and/or surgical tasks are performed on the anatomical structure.

In practice, a target view of the anatomical structure may be a view delineated during a planning phase of an endoscopic procedure or identified by a clinician during the navigation phase of the endoscopic procedure.

Also in practice, a degree of correlation dictates whether a single guided manipulation anchor or a single set of guided manipulation anchors are needed for representing location marking(s) and motion directive(s) of guided manipulation(s) of the anatomical structure, or whether a temporal series of guided manipulation anchors are needed for representing a temporal series of location markings and motion directive of guided manipulations of the anatomical structure.

Still referring to FIG. 1, the manipulative guidance controller may receive the endoscopic view of the anatomical structure or may ascertain the endoscopic view of the anatomical structure from a tracked positioning of an endoscope relative to a partial or whole volume scan of an anatomical structure.

Examples of images corresponding to the endoscopic based procedure include, but are not limited to, volumetric scans, pre-operative or intra-operative, of an anatomical region (e.g., a CT scan, a MRI scan, a PET scan, a 3D ultrasound scan, a 3D X-ray scan).

Examples of models corresponding to the endoscopic based procedure include, but are not limited to, three-dimensional representations of an anatomical structure (e.g., anatomical models generated via subtractive or additive manufacturing in accordance with an anatomical atlas).

Examples of detail(s) corresponding to the anatomical structure include but are not limited to, biological properties of the anatomical structure and endoscopic procedural steps associated with the anatomical structure.

Still referring to FIG. 1, in practice, endoscopic viewing controller 20 and manipulative guidance controller 30 may be segregated as shown, partially integrated or wholly integrated.

In a first exemplary embodiment as shown in FIG. 2A, an endoscopic viewing controller 20a generates an endoscopic view 11a of an anatomical structure from an endoscope 10a as known in the art of the present disclosure. Endoscopic viewing controller 20a employs a guidance planner 21 for generating a planned view of the anatomical structure via a volume scan of an anatomical region as known in the art of the present disclosure or hereinafter conceived, and an image guide 22 for controlling a display of endoscopic view 11a of an anatomical structure on a monitor 70 via a display controller 60a as known in the art of the present disclosure or hereinafter conceived. The display of endoscopic view 11a may be adjacent to or overlaid upon a display of the volume scan of the anatomical region.

A manipulative guidance controller 30a receives endoscopic view 11a of the anatomical structure from endoscopic viewing controller 20a as shown or alternatively ascertains endoscopic view 11a of the anatomical structure from a tracking of endoscope 10a relative to the volume scan of the anatomical region. Manipulative guidance controller 30a generates a guided location manipulation anchor(s) 50a, guided motion manipulation anchor(s) 51a and/or guided positioning manipulation anchor(s) 52a by analyzing a correlation of the endoscopic view 11a of the anatomical structure with a knowledge base 40 including image(s) 41 of the anatomical structure, anatomical model(s) 42 of the anatomical structure, an image compilation 42 of the anatomical structure, salient feature information 43 of the anatomical structure and/or a planned navigation 44 of endoscope 10a relative to the anatomical structure. As will be further described in the present disclosure, manipulative guidance controller 30a derives the guided manipulation anchor(s) based on a degree of correlation of the endoscopic view 11a of the anatomical structure with the knowledge base 40.

Manipulative guidance controller 30a controls a display of guided location manipulation anchor(s) 50a, guided motion manipulation anchor(s) 51a and/or guided positioning manipulation anchor(s) 52a within a display of endoscopic view 11a of an anatomical structure on monitor 70 via display controller 60a as known in the art of the present disclosure or hereinafter conceived.

In a second exemplary embodiment as shown in FIG. 2B, an endoscopic viewing controller 20b generates an endoscopic view 11a of an anatomical structure from an endoscope 10a as known in the art of the present disclosure. Endoscopic viewing controller 20b employs a guidance planner 21 for generating a planned view of the anatomical structure via a volume scan of an anatomical region as known in the art of the present disclosure or hereinafter conceived, and an image guide 22 for controlling a display of an endoscopic view 11b of an anatomical structure on monitor 70 via a display controller 60b as known in the art of the present disclosure or hereinafter conceived. The display of endoscopic view 11b may be adjacent to or overlaid upon a display of the volume scan of the anatomical region.

A manipulative guidance controller 30b receives endoscopic view 11a of the anatomical structure from endoscopic viewing controller 20b as shown or alternatively ascertains endoscopic view 11a of the anatomical structure from a tracking of endoscope 10a relative to the volume scan of the anatomical region. Manipulative guidance controller 30b generates a guided location manipulation anchor(s) 50b, guided motion manipulation anchor(s) 51b and/or guided positioning manipulation anchor(s) 52b by analyzing a correlation of the endoscopic view 11a of the anatomical structure with a knowledge base 40 including image(s) 41 of the anatomical structure, anatomical model(s) 42 of the anatomical structure, an image compilation 42 of the anatomical structure, salient feature information 43 of the anatomical structure and/or a planned navigation 44 of endoscope 10a relative to the anatomical structure. As will be further described in the present disclosure, manipulative guidance controller 30a derives the guided manipulation anchor(s) based on a degree of correlation of the endoscopic view 11a of the anatomical structure with the knowledge base 40.

Manipulative guidance controller 30b communicates the guided manipulation anchor(s) to endoscopic imaging controller 20b, whereby image guide 22 controls a display of guided location manipulation anchor(s) 50b, guided motion manipulation anchor(s) 51b and/or guided positioning manipulation anchor(s) 52b within a display of endoscopic view 11b of an anatomical structure on monitor 70 via display controller 60b as known in the art of the present disclosure or hereinafter conceived.

In a third exemplary embodiment as shown in FIG. 2C, an endoscopic viewing controller 20c generates an endoscopic view 11a of an anatomical structure from an endoscope 10a as known in the art of the present disclosure. Endoscopic viewing controller 20c employs a guidance planner 21 for generating a planned view of the anatomical structure via a volume scan of an anatomical region as known in the art of the present disclosure or hereinafter conceived, and an image guide 22b for controlling a communication of endoscopic view 11a to manipulative guidance controller 30c.

Manipulative guidance controller 30c receives endoscopic view 11a of the anatomical structure from endoscopic viewing controller 20c as shown and generates a guided location manipulation anchor(s) 50c, guided motion manipulation anchor(s) 51c and/or guided positioning manipulation anchor(s) 52c by analyzing a correlation of the endoscopic view 11a of the anatomical structure with a knowledge base 40 including image(s) 41 of the anatomical structure, anatomical model(s) 42 of the anatomical structure, an image compilation 42 of the anatomical structure, salient feature information 43 of the anatomical structure and/or a planned navigation 44 of endoscope 10a relative to the anatomical structure. As will be further described in the present disclosure, manipulative guidance controller 30c derives the guided manipulation anchor(s) based on a degree of correlation of the endoscopic view 11a of the anatomical structure with the knowledge base 40.

Manipulative guidance controller 30c communicates an endoscopic view 11c of an anatomical structure with overlaid guide manipulation anchors to a display controller 60c for display on monitor 70 via a display controller 60a as known in the art of the present disclosure or hereinafter conceived. The display of endoscopic view 11c may be adjacent to or overlaid upon a display of the volume scan of the anatomical region.

Figure 3:
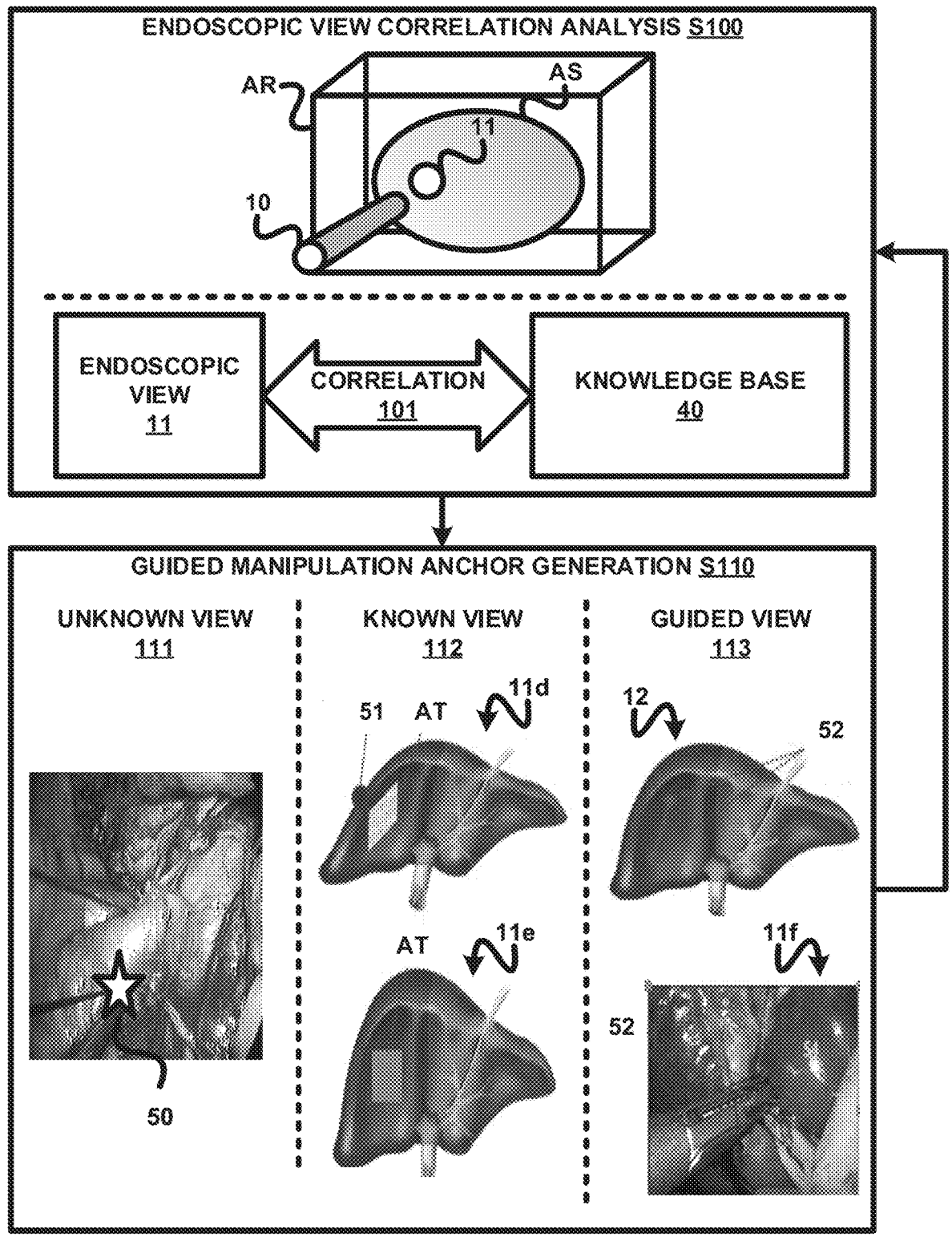
FIG. 3 illustrates an exemplary embodiment of a manipulative guidance method in accordance with the present disclosure executable by the manipulative endoscopic guidance device of FIGS. 2A-2C.

To further facilitate an understanding of a guided manipulation of the present disclosure, the following description of FIG. 3 teaches respective exemplary embodiments of a manipulative endoscopic guidance method in accordance with the present disclosure. From the description of FIG. 3, those having ordinary skill in the art of the present disclosure will appreciate how to apply the present disclosure to make and use additional embodiments of manipulative endoscopic guidance methods in accordance with the present disclosure.

Referring to FIG. 3, a manipulative endoscopic method of the present disclosure during an endoscopic procedure involves a manipulative guidance controller of the present disclosure executing an endoscopic view correlation analysis S100 of unmanipulated anatomical structure AS as an endoscope 10 is focused or navigated within an anatomical region AR and a guided tool manipulation anchor generation S110 of display of guided manipulative anchor(s) on the endoscope view 11 of an anatomical structure AS as needed.

These stages S100 and S110 are continuously repeated as necessary by the manipulative guidance controller, depending on the goal of the guidance, where the anatomical structure is altered in accordance with the guided manipulative anchor(s). For example, if the goal is to reconstruct a large field of view of the anatomical structure AS, then the manipulative guidance controller will repeatedly show manipulation suggestions until it acquires enough views to stitch together a full view of the anatomical structure AS In practice of stages S100 and S110, the manipulative guidance controller first analyzes the present instantaneous endoscope view 11. If the manipulative guidance controller does not have a complete understanding of what is in the endoscopic view 11 (i.e., an unknown view 111), then the manipulative guidance controller generates guided manipulation anchor(s) and overlays the anchor(s) onto the endoscope view 11, so that the clinician knows where to perform the guided manipulation. The clinician may carry out the indicated guided manipulation, thus putting the anatomical structure AS in the view to a known or recognizable state. The state of knowing may be visual, tactile (through force sensing), or other measures engaged by the clinician in the act of manipulating the anatomical structure AS. The manipulative guidance controller then analyzes and incorporates the new information revealed into knowledge base 40, which the manipulative guidance controller subsequently draws upon to guide the clinician later in the procedure.

An example of knowledge base 40 is a preoperative volume scan (e.g., a CT scan or a MRI can), which captures a state of the anatomical structure AS at a point of time before the procedure. The mapping between a preoperative volume scan and an endoscope image may not be fully known at the start of surgery for a variety of reasons. For example, the images are acquired using different modalities, so the images capture similar information in different ways, which have to be resolved. By further example, the state of the anatomical region AR changes between preoperative and intraoperative states via processes such as deformation or body position, which have to be resolved. Intraoperative view in the endoscope does not capture the full anatomical structure AS under consideration and may be ambiguous as to a relation to the preoperative volume scan, in which case more views must be acquired intraoperatively to match endoscopic images to the preoperative counterpart.

Knowledge base 40 may also be sourced from past data. The data may be a statistical compilation or learned using machine learning techniques. The data may include preoperative images, intraoperative images used in surgery, or even non-image data such as forces, task sequences, etc. In other words, information about a patient may be seeded by information sources that come from somewhere other than the patient, and as the surgery progresses the generic information may be tuned to better match the patient.

If the manipulative guidance controller starts with a partial mapping between a preoperative knowledge base 40 and endoscopic view 11, then the manipulative guidance controller may guide the clinician on how to manipulate known anatomical structure AS to expose those parts that yet unknown are unknown to the manipulative guidance controller. This may be of particular value if the clinician is looking for a part of the anatomical structure AS that is not currently in view. As an example, say neither the manipulative guidance controller nor the clinician knows where a major blood vessel is located within anatomical region AR, but based on a knowledge base 40 and current endoscopic view 11, the manipulative guidance controller may infer where the blood vessel may be in anatomical region AR. Then the manipulative guidance controller may guide the clinician on manipulations of the anatomical structure AS that may reveal the hidden vessel. Location markings and motion directives of guided manipulations of anatomical structure AS may be suggested by the manipulative guidance controller in order to reveal visual, tactile, and other forms of anatomical structure AS properties, depending on the sensing elements utilized by manipulative guidance controller.

This manipulative endoscopic guidance method preferably takes place with minimal disruption to the clinician's workflow, i.e., the clinician must be able to perform the procedure naturally without being distracted to respond to the manipulative guidance controller. The manipulative guidance controller also must be able to provide manipulation guidance judiciously by interpreting the state of the procedure or clinician needs.

Still referring to FIG. 3, in the previous embodiment, the manipulative guidance controller does not have complete understanding (e.g., a mapping from live endoscopy to preoperative knowledge base 40), but has enough understanding to guide the clinician on how to manipulate anatomical structure AS to gain a better mapping. In this embodiment, the manipulative guidance controller already recognizes what the manipulative guidance controller sees in the view (e.g., a known view 112), and may thus help guide the clinician on how to manipulate the anatomical structure AS in order for the clinician to recognize what they see.

For example, as shown in stage S110, an endoscopic view 11d of a liver is at an oblique angle, which makes it difficult for the clinician to recognize the liver. This is represented by the oblique shaded square. The manipulative guidance controller understands that a critical vessel or tumor is in that location, and instructs the clinician on where and how to grasp the organ so that stretch the liver whereby the clinician may find see the critical vessel/tumor in an endoscopic view 11e. In this view, the liver is now at an upright facing angle view, making it easier and faster for a clinician to interpret and find clinically relevant features.

Alternatively, the manipulative guidance controller may see the liver at such an oblique angle in endoscopic view 11d of the liver that the manipulative guidance controller cannot precisely recognize the liver or register the liver to knowledge base 40. So the manipulative guidance controller may at least determine the angle that the liver needs to be facing to be more visually recognizable, so it computes a location on the liver for the clinician to grasp and a direction for the clinician to pull. When the clinician proceeds with this guidance, the result is a view that the manipulative guidance controller may recognize with high confidence. This in turn allows the manipulative guidance controller to fuse different information sources into the same view to help clinicians find things further.

In practice, the manipulative guidance controller may need to know a rough location of the anatomical structure AS within the anatomical region AR in order to suggest to the clinician how to manipulate the anatomical structure AS. For example, for endoscopic view 11 may be recognizable by the manipulative guidance controller but insufficient for 3D registration required for 3D overlays, the manipulative guidance controller may implement a base view classifier (e.g., a convolutional neural network) may be trained as known in the art of the present disclosure to communicate, such as, for example, "This 2D view requires manipulation of anatomical structure AS roughly at this mark and/or in this direction."

Still referring to FIG. 3, in another exemplary embodiment, the manipulative guidance controller may rely on a judgment of the clinician. More particularly, in a guided view 113 of stage S110, the manipulative guidance controller shows guide manipulation anchors 52 on a preoperative model 12, and the clinician follows that guide in an endoscopic view 11, which has the effect of correlating the preoperative model 12 and endoscopic view 11. While a single such instance may be insufficient to generate a complete mapping or registration between the preoperative model 12 and endoscopic view 11, multiple, carefully planned instances may generate enough corresponding information. Alternatively, a preoperative image be whereby the clinician looks at a raw view of the endoscopic view 11, uses clinical judgement to find the corresponding anchor(s) on the anatomical structure, and then manipulates those anchor(s) to register the endoscopic view 11 to the preoperative image.

As previously described in the present disclosure, the manipulative guidance controller generates guided manipulation anchor(s) for guiding manipulation of anatomical structure AS manipulation by examining the anatomical structure AS and correlating it to a knowledge base 40. The assumption is that there is an overlap of information, but the connection between endoscopic view 11 and the knowledge base 40 may be incomplete. The manipulative guidance controller then uses what it knows to guide the clinician to reveal what it does not know, to improve its knowledge base 40. In this case, the manipulative guidance controller has partial information.

In the case where the manipulative guidance controller has full information in one modality (e.g., endoscopy and preoperative images), then the manipulative guidance controller may use that knowledge to generate guided manipulation anchor(s) for anatomical structure AS manipulation guidance in order to gain further data of a different modality (e.g., force).

As previously described in the present disclosure, knowledge base 40 may have numerous and various sources of information that may be used to generate a new set of guided manipulation anchor(s). Examples of these sources includes, but are not limited to, preoperative and intraoperative images, information on anatomical structure non-image in nature, statistical compilations of images from past procedures, and knowledge that is learned from past procedures.

The anchors may also be seeded by the clinician using an interactive virtual marking system. In this embodiment, the manipulative guidance controller does not have complete information about the anatomical region, but it may have some loosely coupled preoperative information. The clinician may then use an instrument to label some features they see on the anatomical structure AS, and the virtual labels may be incorporated into the knowledge base 40, allowing the manipulative guidance controller to provide image and manipulation guidance later on in the surgery.

For example, the manipulative guidance controller may incorporate interactive labeling system as known in the art of the present disclosure or hereinafter conceived whereby the clinician uses an instrument to virtually mark and label the anatomical structure AS in the endoscopic view 11 (e.g., a marking via stars indicating locations of a tumor margin, an airway and a vessel). The manipulative guidance controller may then combine this knowledge in real time with its existing knowledge base 40 to provide further anatomical structure manipulation guidance.

In practice, the manipulative guidance controller may generate guided manipulation anchors for the clinician without having semantic information as well. In an embodiment, the manipulative guidance controller detects salient image patterns of interest. Examples of salient patterns include, but are not limited to, high texture areas, areas of common texture or appearance, areas of high contrast compared to its neighbors, patterns that have not been seen before, patterns that have been seen before, patterns that have been seen repeatedly, areas adjacent to areas that are semantically identifiable, and so on. More particularly, the trackable patterns in the anatomical structure AS may be found using a well-known algorithm (e.g., SURF) and the manipulative guidance controller finds a persistent label for these areas. These labels may be refined further to decide on which are to become guided manipulation anchors, as mentioned above.

Still referring to FIG. 3, the practice of stages S100 and S110 is an endoscopic procedure includes an initial planning phase involving a pre-operative or an intra-operative volume scan of anatomical structure AS within anatomical region AR. From the volume scan, the clinician utilizes endoscopic viewing controller 20 or other controller as known in the art of the present disclosure to identify one or more target view(s) within the volume scan of anatomical structure AS for performing a diagnosis, a treatment or a surgery. Depending on the state of the anatomical structure and the goal of the endoscopic procedure, an entirety of the target view may or may not be viewable by an endoscope 10 when endoscope 10 is positioned within a patient.

More particularly, a planning interface as known in the art of the present disclosure may be used for viewing and annotating 2D and 3D data for the purpose of ascertaining target view(s) of the anatomical structure during the procedure. This may be done intra-operatively in the endoscope view involving a fusion of an endoscopic image and volume image, because such an endoscope plan may be done on volumetric image of patient anatomy considering geometries of anatomy and kinematics of the endoscope and other constraints in the clinician preferences. For example, a trocar position relative to the target organ (between the ribs) and geometry and motions of the endoscope (for straight endoscopes it will be the set of positions govern by rotation about the trocar entry point).

The planning phase further involves updating knowledge base 40 of manipulative guidance controller 30 with volume scan of the anatomical structure AS, a planned path, salient feature(s) of the anatomical structure and a task sequence whereby, prior to or concurrently with endoscope 10 being navigated within the anatomical region manipulative guide controller 30 may (1) ascertain a degree to which a target view will be visible to endoscope 10 and/or (2) ascertain one or more recognizable poses of a target view.

After the planning phase, the endoscopic procedure includes a navigation phase of endoscope 10 within the patient P whereby manipulative guidance controller 30 is correlating, to a highest degree possible, the endoscopic view of the anatomical region as the endoscope 10 is being navigated to a position relative to a target view.

One correlation embodiment encompasses manipulative guidance controller 30 attempting to ascertain, to a highest degree possible, the endoscopic view matching the target view within the volume scan stored within the knowledge base 40 as the endoscope 10 is being navigated to a position relative to a target view. Once positioned, if manipulative guidance controller 30 recognizes the endoscopic view matching the target view within the volume scan stored within the knowledge base 40, then manipulative guidance controller 30 will either generate guided manipulation anchors to expose invisible aspects of the anatomical structure or generate guided manipulation anchors to adjust a view of visible aspects of the anatomical structure.

Alternatively, a model of the anatomical structure or a compilation of images may be used in lieu of the volume scan.

Another correlation embodiment encompasses an attempted tracking, to the highest degree possible, of the endoscope navigated to a position relative to a target view. Once manipulative guidance controller 30 determines the endoscope reaches such a position per the planned path or tasks sequence in the knowledge base, if manipulative guidance controller 30 recognizes the endoscopic view matching the target view within the volume scan stored within the knowledge base 40, then manipulative guidance controller 30 will either then manipulative guidance controller 30 will either generate guided manipulation anchors to expose invisible aspects of the anatomical structure or generate guided manipulation anchors to adjust a view of visible aspects of the anatomical structure.

Again, alternatively, a model of the anatomical structure or a compilation of images may be used in lieu of the volume scan.

Another correlation embodiment encompasses an attempted identification, to the highest degree possible, of salient features of the anatomical structure adjacent the target view. Once manipulative guidance controller 30 determines the endoscope reaches such a position per the planned path or tasks sequence in the knowledge base, if manipulative guidance controller 30 recognizes the endoscopic view showing the salient features of the anatomical structure adjacent the target view within the volume scan stored within the knowledge base 40, then manipulative guidance controller 30 will either then manipulative guidance controller 30 will either generate guided manipulation anchors to expose invisible aspects of the anatomical structure or generate guided manipulation anchors to adjust a view of visible aspects of the anatomical structure.

Again, alternatively, a model of the anatomical structure or a compilation of images may be used in lieu of the volume scan.

Figure 4:
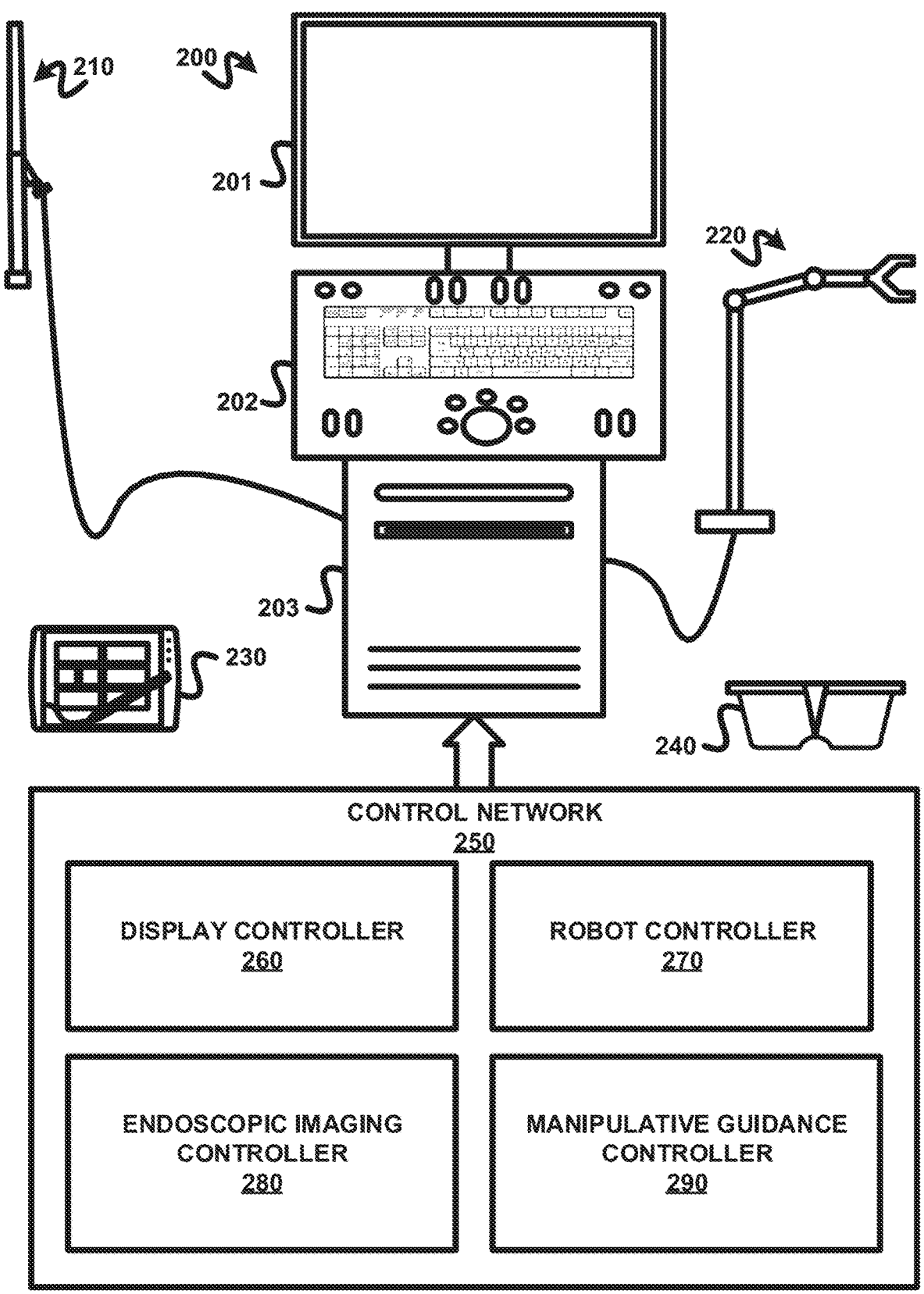
FIG. 4 illustrates an exemplary embodiment of a manipulative endoscopic guidance system in accordance with the present disclosure incorporating the manipulative endoscopic guidance device of FIG. 1.
Figure 5:
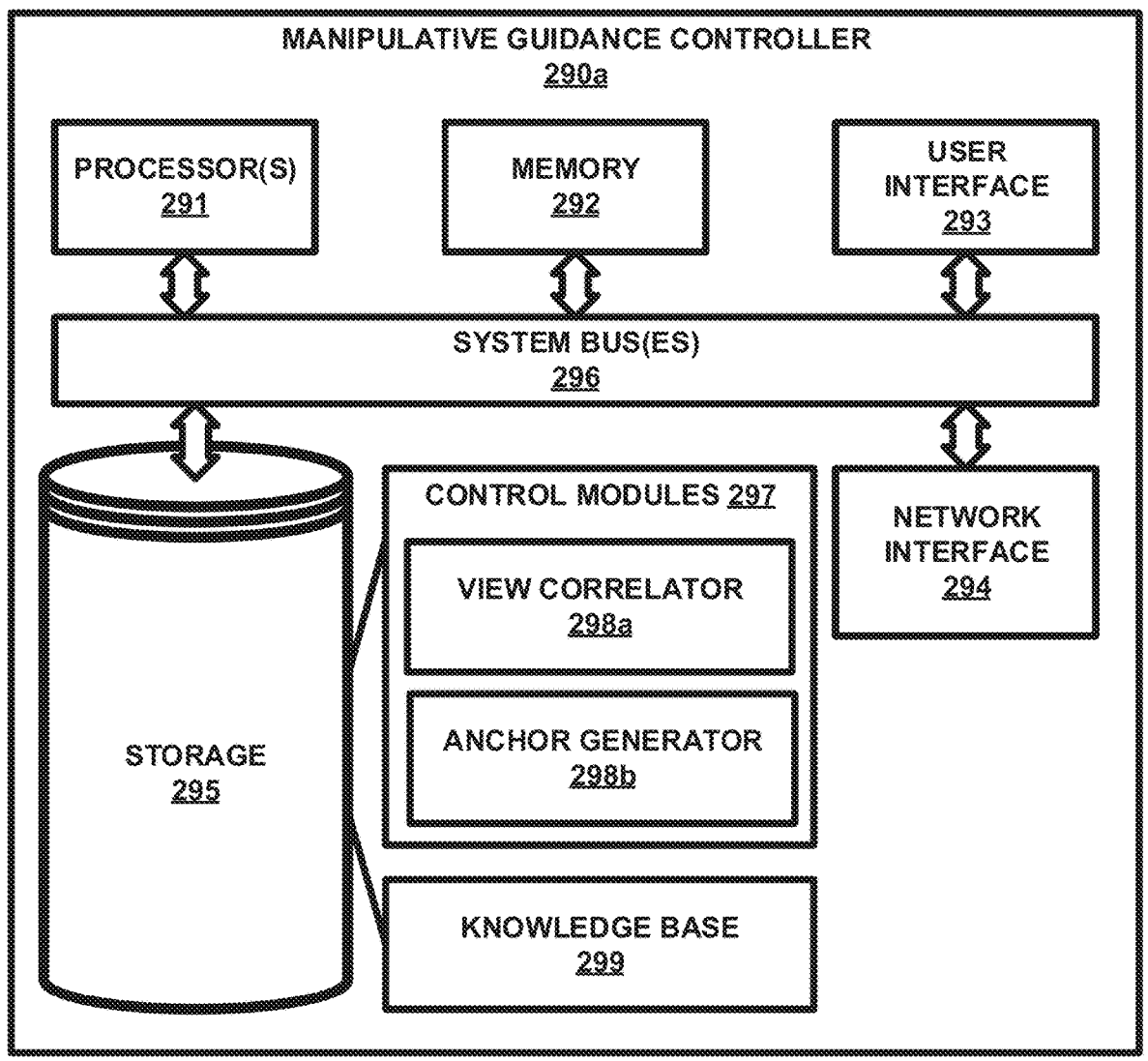
FIG. 5 illustrates an exemplary embodiment of a manipulative guidance controller in accordance with the present disclosure.

To facilitate a further understanding of a guided manipulation of the present disclosure, the following description of FIGS. 4 and 5 respectively teaches exemplary embodiments of a manipulative endoscopic guide system and a manipulative guidance controller of the present disclosure. From this description, those having ordinary skill in the art will appreciate how to apply various aspects of the present disclosure for making and using additional embodiments of manipulative endoscopic guide devices and manipulative guidance controllers of the present disclosure.

Referring to FIG. 4, in one exemplary embodiment, a manipulative endoscopic guide system of the present disclosure is a workstation 200 employing a monitor 201, a keyboard 202 and a computer 203 as known in the art of the present disclosure. An endoscope 210 is in communication, wired or wireless, with workstation 200 as known in the art of the present disclosure or hereinafter received. An optional robot 220 for performing guided manipulations may also be communication, wired or wireless, with workstation 200.

A control network 250 of a display controller 260 as known in the art of the present disclosure or hereinafter conceived, a robot controller 270 as known in the art of the present disclosure or hereinafter conceived, an endoscopic imaging controller 280 as previously described in the present disclosure and a manipulative guidance controller 290 as previously described in the present disclosure are installed in workstation 200. Additional control networks 250 may be also be installed in a server (not shown), a mobile device (e.g., a tablet 230 as shown) and an augmented reality device (e.g., a head mounted display 240 as shown).

Still referring to FIG. 4, in practice, the specific mechanism involved to effect guided manipulation may serve as a basis on a determination on how the guidance is communicated to the clinician. For example, manual or robotic instruments (e.g., robot 220) may be used in an equivalent manner to grasp tissue based on guidance.

More particularly, the motion may assisted such that it is semi-automatic. For example with robotic tools, the clinician only needs to bring an end effector to the general region of the guided manipulative anchor, and then the robot can automatically perform the remainder of the grasp and manipulation as known in the art of the present disclosure.

In one exemplary embodiment, magnetic devices as known in the art of the present disclosure or hereinafter conceived may be used to effect guided manipulation. For example, Levita® Magnetics commercially provides a magnetic surgical platform including a magnetic module that sits on top of the patient's abdomen and a ferromagnetic module clip attached to the portion of the tissue to be pulled. This clip is inserted through surgical ports and deployed by clamping to the tissue to be held. The magnetic module is then placed on top of the patient's abdomen, attracting the ferromagnetic module towards the magnetic module the process, thereby holding the tissue suspended to expose other tissue.

In practice, where there are multiple methods to grasp and move anatomical structure(s) (e.g., tissue), guided manipulation anchors may be shown in a way that distinguishes which type of method(s) should be used for a given grasp instance. This is also a way manipulative guidance controller 290 may predict a result of the grasp maneuver, based on the grasping mechanism used. Manipulative guidance controller 290 further remind the clinician that detachable clips are in place, and may instruct the clinician on how to move the magnetic module to achieve a grasp maneuver.

Referring to FIG. 5, a manipulative guidance controller 290a is an exemplary embodiment of manipulative guidance controller 290 (FIG. 4) including one or more processor(s) 291, memory 292, a user interface 293, a network interface 294, and a storage 295 interconnected via one or more system buses 296.

Each processor 291 may be any hardware device, as known in the art of the present disclosure or hereinafter conceived, capable of executing instructions stored in memory 292 or storage or otherwise processing data. In a non-limiting example, the processor(s) 291 may include a microprocessor, field programmable gate array (FPGA), application-specific integrated circuit (ASIC), or other similar devices.

The memory 292 may include various memories, as known in the art of the present disclosure or hereinafter conceived, including, but not limited to, L1, L2, or L3 cache or system memory. In a non-limiting example, the memory 292 may include static random access memory (SRAM), dynamic RAM (DRAM), flash memory, read only memory (ROM), or other similar memory devices.

The user interface 293 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 294.

The network interface 294 may include one or more devices, as known in the art of the present disclosure or hereinafter conceived, for enabling communication with other hardware devices. In a non-limiting example, the network interface 294 may include a network interface card (NIC) configured to communicate according to the Ethernet protocol. Additionally, the network interface 294 may implement a TCP/IP stack for communication according to the TCP/IP protocols. Various alternative or additional hardware or configurations for the network interface 294 will be apparent.

The storage 295 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 295 may store instructions for execution by the processor(s) 291 or data upon with the processor(s) 291 may operate. For example, the storage 295 may store a base operating system for controlling various basic operations of the hardware. The storage 295 also stores application modules in the form of executable software/firmware for implementing the various functions of the manipulative guidance controller 290a as previously described in the present disclosure including, but not limited to, a view correlator 298a and an anchor generator 298b. Storage S295 also stores a knowledge base 299 in accordance with the various embodiments of knowledge bases as previously described in the present disclosure.

Figure 6:
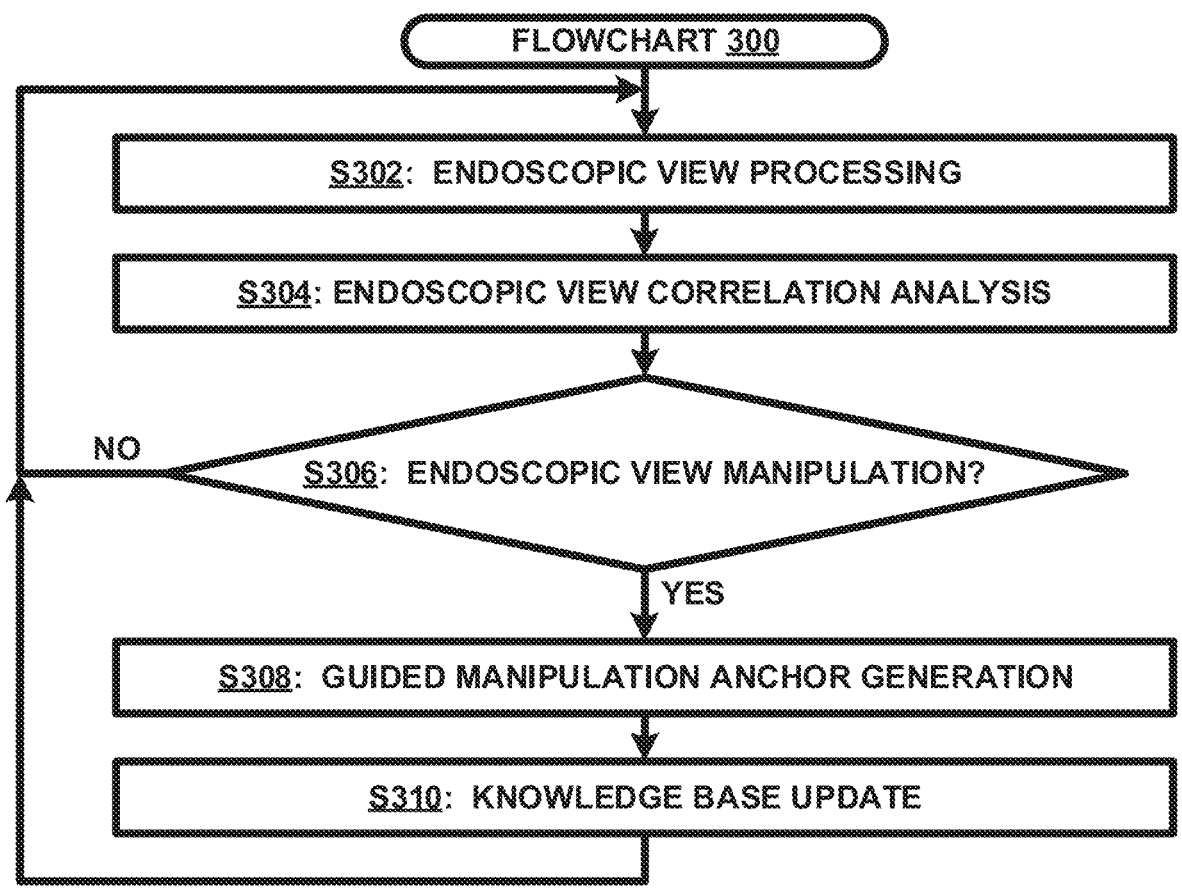
FIG. 6 illustrates a flowchart representative of an exemplary embodiment of a manipulative guidance method in accordance with the present disclosure executable by the manipulative guidance controller of FIG. 4.

FIG. 6 illustrate a flowchart 300 representative of a manipulative guidance method of the present discloses executable by view correlator 298a and anchor generator 298b of FIG. 5.

Referring to FIG. 6, a stage S302 of flowchart 300 involves view correlator 298a receiving or identifying an endoscopic view of an anatomical structure as previously described in the present disclosure, and a stage S304 of flowchart 300 involves view correlator 298a performing an endoscopic view correlation analysis of an endoscopic view of an anatomical structure as previously described in the present disclosure. More particularly, view correlator 298a relates, to the best degree possible, the endoscope view to a knowledge base of images(s), model(s) and/or procedure detail(s) of the endoscopic procedure. For example, view correlator 298 determines, to the best degree possible, a position of endoscopic view of an anatomical structure within a volume scan of an anatomical region or on an anatomical model via registration techniques as known in the art of the present disclosure or from a tracking of the endoscope indicative of a camera positioning of the endoscope relative to the anatomical region.

Still referring to FIG. 6, view correlator 298a will remain in a loop of stages S302 and S304, and upon a trigger of an endoscopic view manipulation of stage S306 of flowchart 300, a stage S308 of flowchart 300 involves anchor generator 298b generating guided manipulation anchor(s) previously described in the present disclosure, and a stage S310 of flowchart of flowchart 300 involves anchor generator 298b updating the knowledge base based on a manipulation of the anatomical structure.

The preceding description of FIGS. 1-6 teaches the various principles of the present disclosure for displaying guided manipulation anchors exclusive of a guided visualization of an anatomical feature of interest.

The following description of FIGS. 7-14 teaches the various principles of the present disclosure for displaying guided manipulation anchors inclusive of a guided visualization of an anatomical feature of interest.

More particularly, the present disclosure improves upon the prior art of endoscopic procedures by providing guided visualizations for a clinician (e.g., a radiologist, a therapist or a surgeon) on a position of anatomical feature of interest hidden from an endoscopic view of an anatomical structure (e.g., tissue, bone, nerves and blood vessels).

For purposes of describing and claiming the present disclosure, the term "hidden feature" broadly encompasses any targeted characteristic piece, portion, section, segment, etc. of an anatomical structure hidden from endoscopic view by other characteristic piece, portion, section, segment, etc. of the anatomical structure and/or hidden from endoscopic view by additional anatomical structure(s).

One objective of a guided visualization of the present disclosure is a manipulated exposure of the hidden feature of the anatomical structure in a known, baseline, or recognizable state within the endoscopic view for facilitating a diagnostic analysis, a therapeutic treatment and/or a surgical operation of the partial or fully exposed hidden feature of the anatomical structure within the endoscopic view.

For purposes of describing and claiming the present disclosure, the term "guided visualization" broadly encompasses, as known in the art of the present disclosure and hereinafter conceived, a graphical indication of a position of an anatomical feature of interest within an anatomical structure relative to an endoscopic view of the anatomical structure.

A non-limiting example of a guided visualization of the present disclosure is an anchor having a shape, a color and/or a size informative of a two-dimensional or a three-dimensional directional vector from the pose of the endoscopic view of the anatomical structure to the position of the hidden feature within the anatomical structure. As such, the anchor may change shape, color and/or size as a pose of the endoscopic view of the anatomical structure is altered relative to the position of the hidden feature within the anatomical structure.

For purposes of describing and claiming the present disclosure, again the term "anchor" broadly encompasses a visual representation, as known in the art of the present disclosure and hereinafter conceived, for continually marking a specific location within view of an imaging modality, and the term "hidden feature anchor" broadly encompasses a visual representation, in accordance with the present disclosure, of a position of a hidden anatomical feature of interest whereby a clinician (e.g., a radiologist, a therapist or a surgeon) may visualize a context of the diagnostic, therapeutic and/or surgical guidance of tools and instruments to the anatomical feature of interest.

In practice, a hidden feature anchor of the present disclosure may be overlaid on an endoscopic video feed whereby the anchor is a static visual augmentation on any type of physical, virtual or augmented display (e.g., display monitors, head mounted displays, etc.). Additionally, the display may render a 3D model of the scene if such data is available. A hidden feature anchor of the present disclosure may also be dynamic whereby the guided manipulation anchor appears to adhere to the associated anatomical structure (e.g., tissue, bone, nerves and blood vessels).

For example, the hidden feature anchor may track with the underlying tissue as that tissue moves or is deformed. Consequently, the hidden feature anchor may disappear if the tissue goes out of the endoscopic view and reappear if the tissue comes back into the endoscopic view.

Further in practice, visually, a hidden feature anchor of the present disclosure may be opaque to grab the clinician's attention, or translucent to allow vison by the clinician to the anatomical structure(s) behind the hidden feature anchor. Hidden feature anchor of the present disclosure may also vary by the nature of the anchors (e.g., informative or query within a context of the diagnostic, therapeutic and/or surgical endoscopic procedure). The shapes, colors, and sizes of a hidden feature anchor of the present disclosure may be similarly adjusted to communicate messages. For examples, a shape of a guided manipulation anchor of the present disclosure may be oriented to communicate a degree of exposure or a degree of concealment of the anatomical feature of interest.

Also in practice, hidden features anchors of the present disclosure may be communicated through means beyond visualization. For example, a haptic display maybe shaped or colored or a haptic joystick may be vibrated to communicate to the clinician that the instrument location is a proximate to the position of the anatomical feature of interest. Other nonlimiting communication means include audible cues and combinations of haptic stimuli.

Additionally in practice, directionality of anatomical manipulation may be determined based on a combination of the directional vector of the endoscopic view to the position of the hidden feature of the anatomical structure and the immediate task(s) to be performed during the endoscopic procedure and. For example, if tissue to be grasped is an edge of an organ, then a direction should be into the organ for a folding motion and outward for a stretching motion that facilitates an exposure of the hidden anatomical feature. An embodiment of determining tissue characteristics may involve torsion motion of the tissue grasp as well to thereby allow for an execution of a desired motion in a preferred direction of the hidden anatomical feature.

More particularly, a direction of anatomical manipulation may be computed based on efficient task execution and workflow as well. For example, if it is known that a particular incision is most safely and efficiently performed at a certain angle, then a clinician may be guided on staging the tissue to that angle in pursuit of exposing the hidden anatomical feature. Also, a direction of anatomical manipulation may be computed based on intraoperative criteria such as, for example, current angulation of tissue, camera, and instruments, which also may be extended to one or more sequences of tasks.

Figure 7:
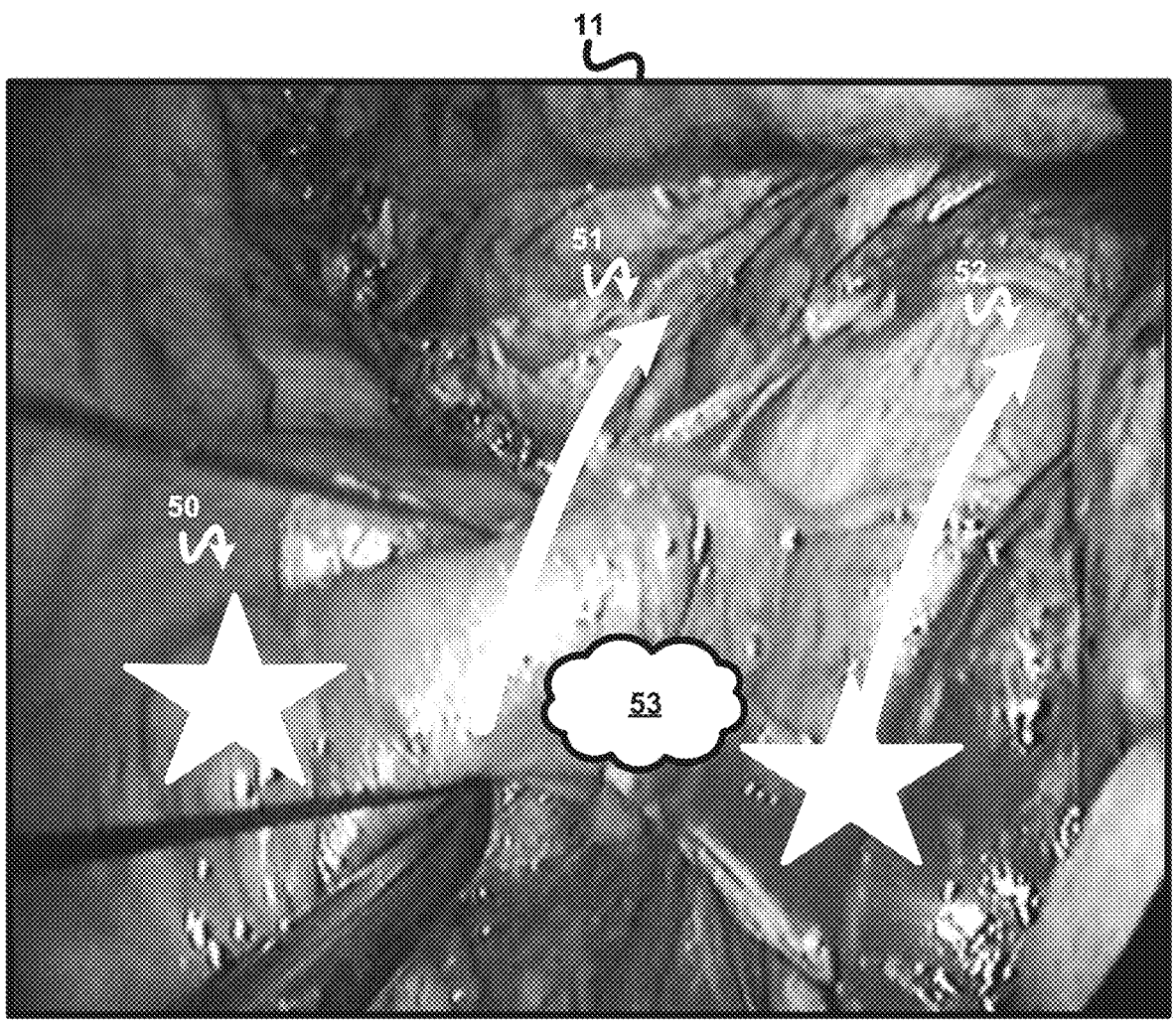
FIG. 7 illustrates an exemplary embodiment of a visual endoscopic guidance device in accordance with the present disclosure.
Figure 8A:
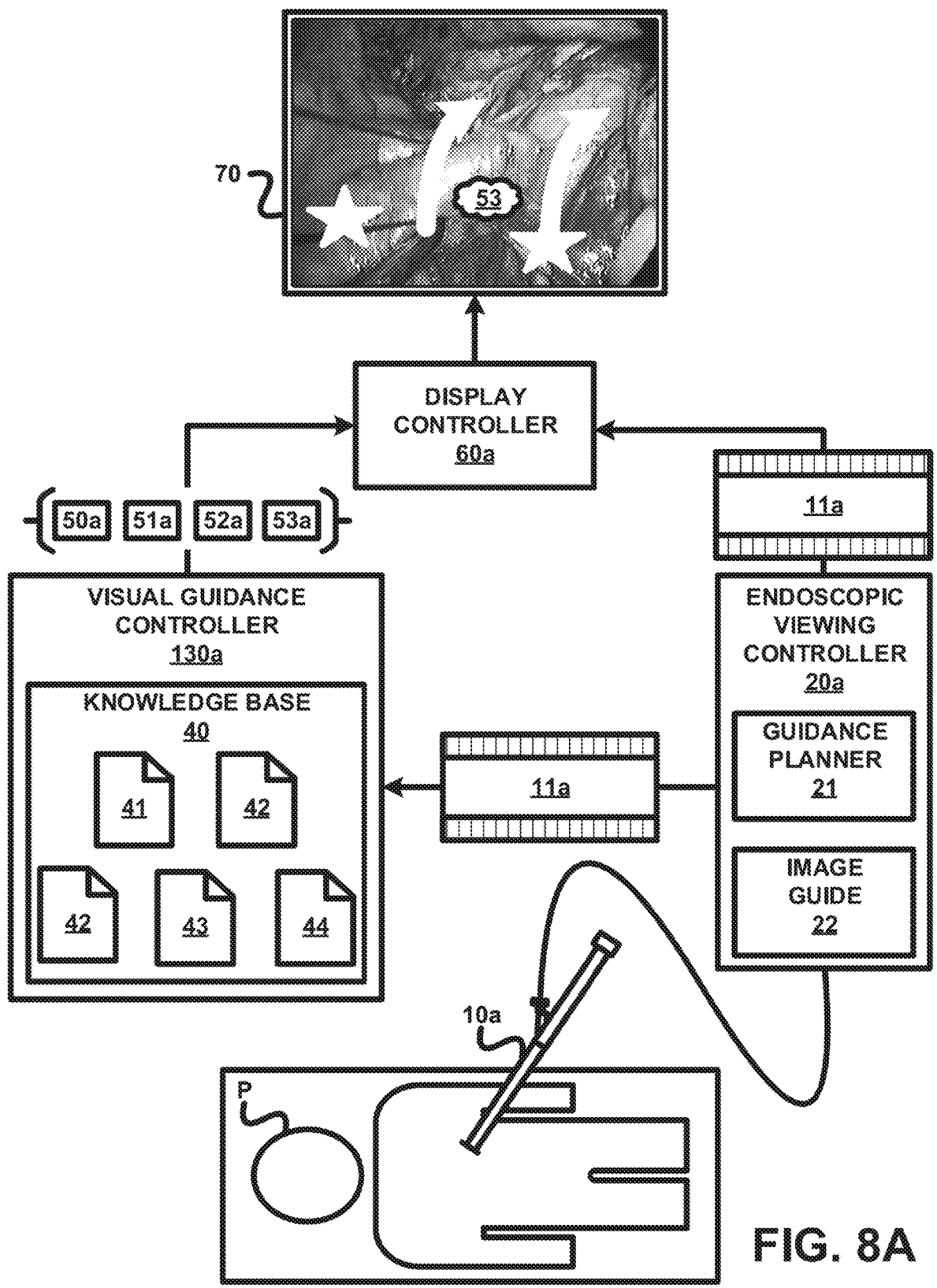
FIGS. 8A-8C illustrate exemplary embodiments of the visual endoscopic guidance device of FIG. 7 in accordance with the present disclosure.
Figure 8B:
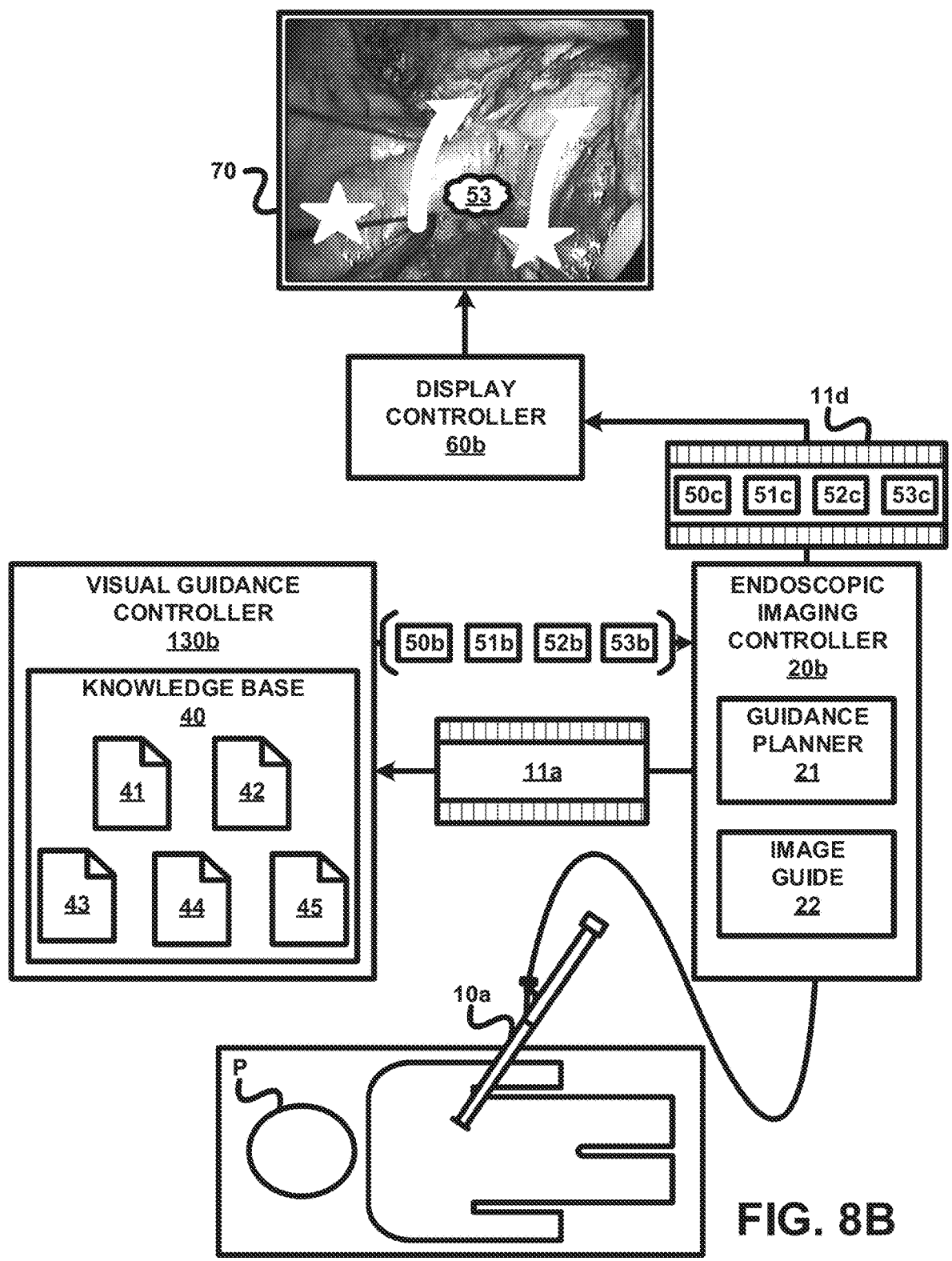
Figure 8C:
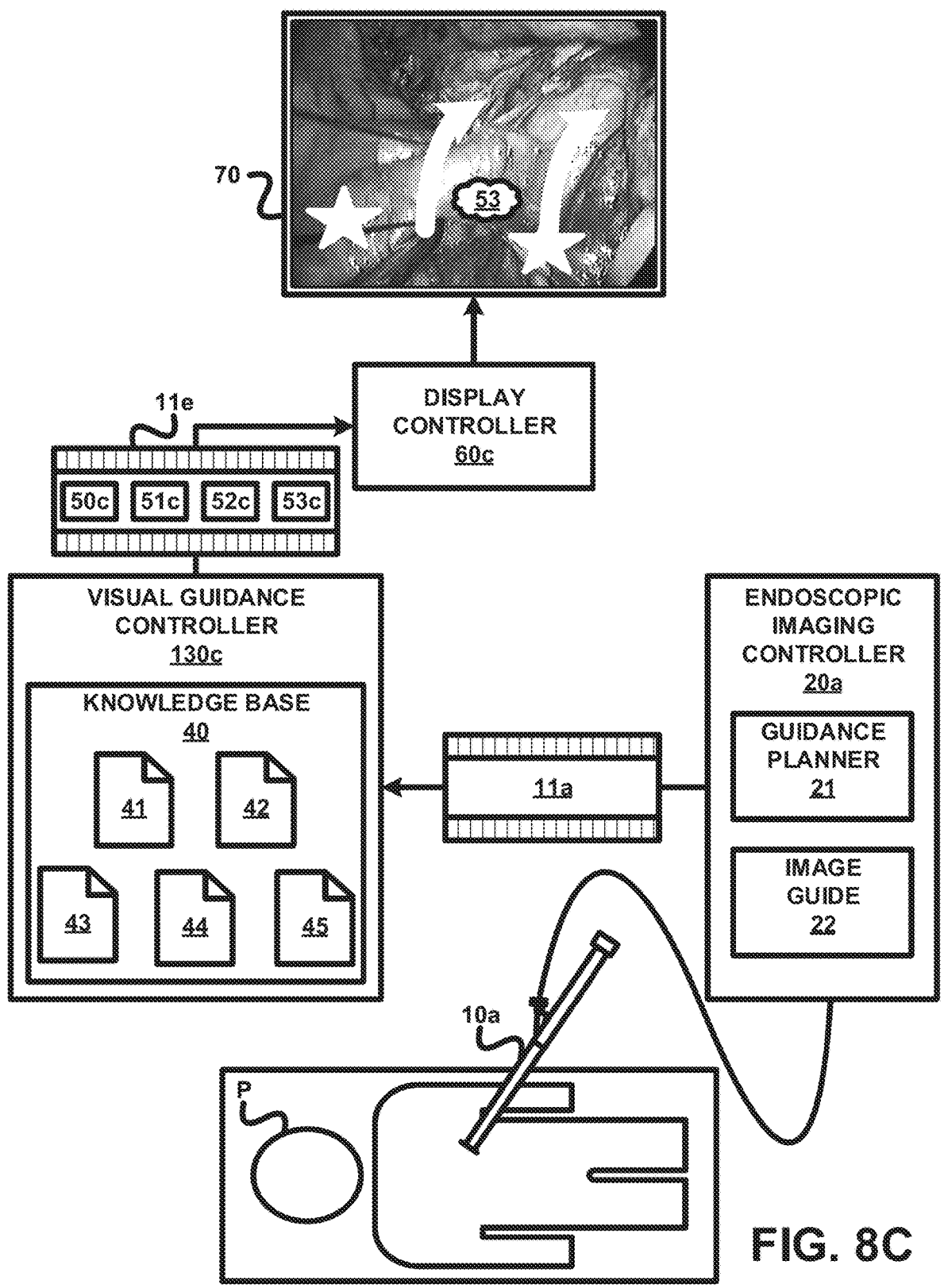

To facilitate an understanding of a guided visualization of the present disclosure, the following description of FIGS. 7-8C teaches respective exemplary embodiments of a visual endoscopic guidance device in accordance with the present disclosure. From the description of FIGS. 7-8C, those having ordinary skill in the art of the present disclosure will appreciate how to apply the present disclosure to make and use additional embodiments of visual endoscopic guidance devices in accordance with the present disclosure.

Referring to FIG. 7, endoscope 10 as previously described for FIG. 1 generates an endoscopic view of the anatomical structure, such as, for example, an endoscopic view 11 of a lung as shown in FIG. 7. Again, examples of the endoscope include, but are not limited to, an anoscope, an arthroscope, a bronchoscope, a colonoscope, a colposcope, a cystoscope, an esophagoscope, a gastroscope, a laparoscope, a laryngoscope, a neuroendoscope, a proctoscope, a sigmoidoscope and a thoracoscope.

The present disclosure provides a visual endoscopic guidance device employing an endoscopic viewing controller 20 as previously described for FIG. 1 and a visual guidance controller 130.

For purposes of describing and claiming the present disclosure, the term "visual guidance controller" encompasses all structural configurations, as understood in the art of the present disclosure and as exemplary described in the present disclosure, of a main circuit board or an integrated circuit for applying various principles of the present disclosure for controlling a display of one or more guided manipulation anchors within a display of an endoscopic view of an anatomical structure and for controlling a display of a hidden feature anchor relative to the endoscopic view of the anatomical structure in accordance with the present disclosure. The structural configuration of the visual guidance controller may include, but is not limited to, processor(s), computer-usable/computer readable storage medium(s), an operating system, application module(s), peripheral device controller(s), slot(s) and port(s).

For purposes of describing and claiming the present disclosure, the term "application module" as related to a visual guidance controller broadly encompasses an application incorporated within or accessible by a visual guidance controller consisting of an electronic circuit (e.g., electronic components and/or hardware) and/or an executable program (e.g., executable software stored on non-transitory computer readable medium(s) and/or firmware) for executing a specific application associated controlling a display of one or more guided manipulation anchors within a display of an endoscopic view of an anatomical structure in accordance with the present disclosure and for controlling a display of a hidden feature anchor relative to the endoscopic view of the anatomical structure in accordance with the present disclosure.

As previously described herein, a guided manipulation anchor is representative of a location marking and/or a motion directive of a guided manipulation of the anatomical structure including, but not limited to, a grasping, a pulling, a pushing, a sliding, a reorienting, a tilting, a removing, and/or a repositioning of the anatomical structure during an endoscopic based diagnostic procedure, an endoscopic based therapeutic procedure and/or an endoscopic based surgical procedure. A clinician (e.g., a radiologist, a therapist or a surgeon) may manually or robotically implement the guided manipulation as displayed, or the visual guidance controller may automatically control robotic instruments to manipulate the tissue accordingly.

For example, as previously described herein, guided manipulation anchor 50 as overlaid on endoscopic view 11 of a lung is representative of a location marking of a guided manipulation of the anatomical structure whereby a shape, a color and/or a size of guided manipulation anchor 50 may expressly communicate a particular type of guided manipulation of the anatomical structure (e.g., a grasping, a pulling, a pushing, a sliding, a reorienting, a tilting, a removing, and/or a repositioning of the anatomical structure).

By further example, as previously described herein, guided manipulation anchor 51 as overlaid on endoscopic view 11 of a lung is representative of a motion directive of a guided manipulation of the anatomical structure whereby a shape, a color and/or a size of guided manipulation anchor 50 may expressly communicate a particular type of guided manipulation of the anatomical structure (e.g., a grasping, a pulling, a pushing, a sliding, a reorienting, a tilting, a removing, and/or a repositioning of the anatomical structure).

By further example, as previously described herein, guided manipulation anchor 52 as overlaid on endoscopic view 11 of a lung is representative of a location marking and a motion directive of a guided manipulation of the anatomical structure whereby a shape, a color and/or a size of guided manipulation anchor 50 may expressly communicate a particular type of guided manipulation of the anatomical structure (e.g., a grasping, a pulling, a pushing, a sliding, a reorienting, a tilting, a removing, and/or a repositioning of the anatomical structure).

Still referring to FIG. 1, a hidden feature anchor is representative of a position (e.g., a location and/or an orientation) of a guided visualization of the hidden feature of the anatomical structure including, but not limited to, an anchor informative of a position of the hidden feature of the anatomical structure relative to an endoscopic view of the anatomical structure or relative to an image map including the endoscopic view of the anatomical structure.

For example, a hidden feature anchor 53 as overlaid on endoscopic view 11 of a lung is representative of a position (e.g., a location and/or an orientation) of a guided visualization of the hidden feature of lung. More particularly a shape, a color and/or a size informative of a two-dimensional or a three-dimensional directional vector from the pose of the endoscopic view 11 of the lung to the position of the hidden feature within the lung.

Still referring to FIG. 1, in practice for guided visualization purposes, visual guidance controller 130 generates guided manipulation anchor(s) relative to a position of a hidden anatomical feature in dependence of the endoscopic view of the anatomical structure in a context of the endoscopic based diagnostic procedure, an endoscopic based therapeutic procedure and/or an endoscopic based surgical procedure.

In one embodiment as will be further described in the present disclosure, visual guidance controller 130 may generate a guided manipulation anchor (1) by analyzing a correlation of the endoscopic view of the anatomical structure with a knowledge base of image(s), model(s) and/or detail(s) corresponding to the anatomical structure; (2) by identifying a position (i.e., location and/or orientation) of the hidden feature within the image(s) and/or the model(s) of the anatomical structure as detailed in the knowledge base; and (3) by deriving the guided manipulation anchor based on a degree of correlation of the endoscopic view of the anatomical structure with the knowledge base the image(s) and/or the model(s) of the anatomical structure as detailed in the knowledge base and a degree of confidence of a determined spatial pose of the endoscopic view of the anatomical structure relative to the position of the hidden feature within the anatomical structure.

In the same embodiment as will be further described in the present disclosure, visual guidance controller 130 may generate a hidden feature anchor by deriving the hidden feature anchor based on a degree of confidence in the identification of the position of the hidden anatomical feature the image(s) and/or the model(s) of anatomical structure as correlated to the endoscopic view of the anatomical structure.

For purposes of describing and claims the present disclosure, the term "correlation" broadly encompasses an endoscopic view having a mutual relationship with a target view of an anatomical structure. Examples of a mutual relationship includes, but is not limited to, (1) an image matching of the endoscopic view to the target view within a volume scan of the anatomical structure, (2) an imaging matching of the endoscopic view to a target view on a model of the anatomical structure, (3) an imaging matching of the endoscopic view to a target view of an image compilation of anatomical structure, (4) an imaging matching of anatomical features illustrated within the endoscopic view to with salient anatomical features illustrated within the target view, and (5) an evolving image matching of the endoscopic view to the target view as treatment tasks and/or surgical tasks are performed on the anatomical structure.

In practice, a target view of the anatomical structure may be a view delineated during a planning phase of an endoscopic procedure or identified by a clinician during the navigation phase of the endoscopic procedure.

Also in practice, a degree of correlation dictates whether a single guided manipulation anchor or a single set of guided manipulation anchors are needed for representing location marking(s) and motion directive(s) of guided manipulation(s) of the anatomical structure, or whether a temporal series of guided manipulation anchors are needed for representing a temporal series of location markings and motion directive of guided manipulations of the anatomical structure.

Still referring to FIG. 7, visual guidance controller 130 may receive the endoscopic view of the anatomical structure or may ascertain the endoscopic view of the anatomical structure from a tracked positioning of an endoscope relative to a partial or whole volume scan of an anatomical structure.

Examples of images corresponding to the endoscopic based procedure include, but are not limited to, volumetric scans, pre-operative or intra-operative, of an anatomical region (e.g., a CT scan, a MRI scan, a PET scan, a 3D ultrasound scan, a 3D X-ray scan).

Examples of models corresponding to the endoscopic based procedure include, but are not limited to, three-dimensional representations of an anatomical structure (e.g., anatomical models generated via subtractive or additive manufacturing in accordance with an anatomical atlas).

Examples of detail(s) corresponding to the anatomical structure include but are not limited to, biological properties of the anatomical structure and endoscopic procedural steps associated with the anatomical structure.

Still referring to FIG. 7, in practice, endoscopic viewing controller 20 and visual guidance controller 130 may be segregated as shown, partially integrated or wholly integrated.

In a first exemplary embodiment as shown in FIG. 8A, an endoscopic viewing controller 20*a* generates an endoscopic view 11*a* of an anatomical structure from an endoscope 10*a* as known in the art of the present disclosure. Endoscopic viewing controller 20*a* employs a guidance planner 21 for generating a planned view of the anatomical structure via a volume scan of an anatomical region as known in the art of the present disclosure or hereinafter conceived, and an image guide 22 for controlling a display of endoscopic view 11*a* of an anatomical structure on a monitor 70 via a display controller 60*a* as known in the art of the present disclosure or hereinafter conceived. The display of endoscopic view 11*a* may be adjacent to or overlaid upon a display of the volume scan of the anatomical region.

A visual guidance controller 130*a* receives endoscopic view 11*a* of the anatomical structure from endoscopic viewing controller 20*a* as shown or alternatively ascertains endoscopic view 11*a* of the anatomical structure from a tracking of endoscope 10*a* relative to the volume scan of the anatomical region. Visual guidance controller 130*a* generates a guided location manipulation anchor(s) 50*a*, guided motion manipulation anchor(s) 51*a* and/or guided positioning manipulation anchor(s) 52*a* in combination with hidden feature anchor 53*a* by analyzing a correlation of the endoscopic view 11*a* of the anatomical structure with a knowledge base 40 including image(s) 41 of the anatomical structure, anatomical model(s) 42 of the anatomical structure, an image compilation 42 of the anatomical structure, salient feature information 43 of the anatomical structure and/or a planned navigation 44 of endoscope 10*a* relative to the anatomical structure. As will be further described in the present disclosure, visual guidance controller 130*a* derives the guided manipulation anchor(s) and the hidden feature anchor based on a degree of correlation of the endoscopic view 11*a* of the anatomical structure with the knowledge base 40, and a determined spatial pose of the endoscopic view of the anatomical structure relative to the position of the hidden feature within the anatomical structure.

Visual guidance controller 130*a* controls a display of guided location manipulation anchor(s) 50*a*, guided motion manipulation anchor(s) 51*a* and/or guided positioning manipulation anchor(s) 52*a* in combination with hidden feature anchor 53*a* within a display of endoscopic view 11*a* of an anatomical structure on monitor 70 via display controller 60*a* as known in the art of the present disclosure or hereinafter conceived.

In a second exemplary embodiment as shown in FIG. 8B, an endoscopic viewing controller 20*b* generates an endoscopic view 11*a* of an anatomical structure from an endoscope 10*a* as known in the art of the present disclosure. Endoscopic viewing controller 20*b* employs a guidance planner 21 for generating a planned view of the anatomical structure via a volume scan of an anatomical region as known in the art of the present disclosure or hereinafter conceived, and an image guide 22 for controlling a display of an endoscopic view 11*b* of an anatomical structure on monitor 70 via a display controller 60*b* as known in the art of the present disclosure or hereinafter conceived. The display of endoscopic view 11*b* may be adjacent to or overlaid upon a display of the volume scan of the anatomical region.

A visual guidance controller 130*b* receives endoscopic view 11*a* of the anatomical structure from endoscopic viewing controller 20*b* as shown or alternatively ascertains endoscopic view 11*a* of the anatomical structure from a tracking of endoscope 10*a* relative to the volume scan of the anatomical region. Visual guidance controller 130*b* generates a guided location manipulation anchor(s) 50*b*, guided motion manipulation anchor(s) 51*b* and/or guided positioning manipulation anchor(s) 52*b* in combination with hidden feature anchor 53*b* by analyzing a correlation of the endoscopic view 11*a* of the anatomical structure with a knowledge base 40 including image(s) 41 of the anatomical structure, anatomical model(s) 42 of the anatomical structure, an image compilation 42 of the anatomical structure, salient feature information 43 of the anatomical structure and/or a planned navigation 44 of endoscope 10*a* relative to the anatomical structure. As will be further described in the present disclosure, visual guidance controller 130*a* derives the guided manipulation anchor(s) based on a degree of correlation of the endoscopic view 11*a* of the anatomical structure with the knowledge base 40, and a determined spatial pose of the endoscopic view of the anatomical structure relative to the position of the hidden feature within the anatomical structure.

Visual guidance controller 130*b* communicates the guided manipulation anchor(s) to endoscopic imaging controller 20*b*, whereby image guide 22 controls a display of guided location manipulation anchor(s) 50*b*, guided motion manipulation anchor(s) 51*b* and/or guided positioning manipulation anchor(s) 52*b* in combination with hidden feature anchor 53*b* within a display of endoscopic view 11*b* of an anatomical structure on monitor 70 via display controller 60*b* as known in the art of the present disclosure or hereinafter conceived.

In a third exemplary embodiment as shown in FIG. 8C, an endoscopic viewing controller 20*c* generates an endoscopic view 11*a* of an anatomical structure from an endoscope 10*a* as known in the art of the present disclosure. Endoscopic viewing controller 20*c* employs a guidance planner 21 for generating a planned view of the anatomical structure via a volume scan of an anatomical region as known in the art of the present disclosure or hereinafter conceived, and an image guide 22*b* for controlling a communication of endoscopic view 11*a* to visual guidance controller 130*c*.

Visual guidance controller 130*c* receives endoscopic view 11*a* of the anatomical structure from endoscopic viewing controller 20*c* as shown and generates a guided location manipulation anchor(s) 50*c*, guided motion manipulation anchor(s) 51*c* and/or guided positioning manipulation anchor(s) 52*c* in combination with hidden feature anchor 53*c* by analyzing a correlation of the endoscopic view 11*a* of the anatomical structure with a knowledge base 40 including image(s) 41 of the anatomical structure, anatomical model(s) 42 of the anatomical structure, an image compilation 42 of the anatomical structure, salient feature information 43 of the anatomical structure and/or a planned navigation 44 of endoscope 10*a* relative to the anatomical structure. As will be further described in the present disclosure, visual guidance controller 130*c* derives the guided manipulation anchor(s) based on a degree of correlation of the endoscopic view 11*a* of the anatomical structure with the knowledge base 40, and a determined spatial pose of the endoscopic view of the anatomical structure relative to the position of the hidden feature within the anatomical structure.

Visual guidance controller 130*c* communicates an endoscopic view 11*c* of an anatomical structure with overlaid guide manipulation anchors and the hidden feature anchor to a display controller 60*c* for display on monitor 70 via a display controller 60*a* as known in the art of the present disclosure or hereinafter conceived. The display of endoscopic view 11*c* may be adjacent to or overlaid upon a display of the volume scan of the anatomical region.

Figure 9:
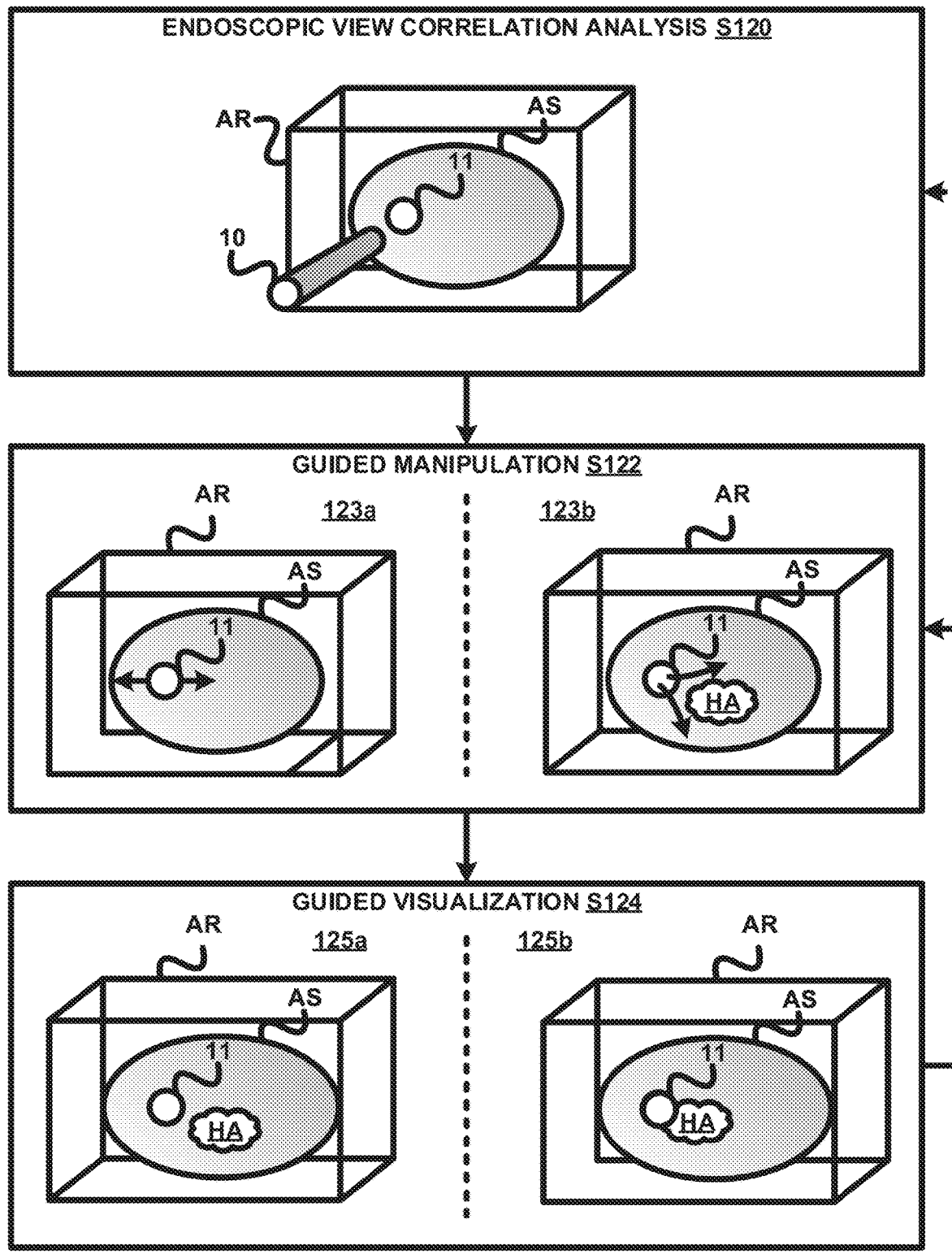
FIG. 9 illustrates an exemplary embodiment of a visual guidance method in accordance with the present disclosure executable by the visual endoscopic guidance device of FIGS. 8A-8C.

To further facilitate an understanding of the present disclosure, the following description of FIG. 9 teaches respective exemplary embodiments of a visual endoscopic guidance method in accordance with the present disclosure. From the description of FIG. 9, those having ordinary skill in the art of the present disclosure will appreciate how to apply the present disclosure to make and use additional embodiments of visual endoscopic guidance methods in accordance with the present disclosure.

Referring to FIG. 9, a visual endoscopic method of the present disclosure during an endoscopic procedure involves a visual guidance controller of the present disclosure executing an endoscopic view correlation analysis S120 of unmanipulated anatomical structure AS as an endoscope 10 is focused or navigated within an anatomical region AR in accordance with a guided manipulation S122 of the anatomical structure and a guided visualization S124 of the hidden anatomical feature.

These stages S120, S122 and S124 are continuously repeated as necessary by the visual guidance controller 130, depending on the goal of the guidance, and where and to what degree the anatomical structure is altered in accordance with the guided manipulative anchor(s) to partially or fully expose the hidden anatomical feature as visualized by the hidden feature anchor. For example, if the goal is to reconstruct a large field of view of the anatomical structure AS to facilitate a view of a partially or fully exposed hidden anatomical feature, then the visual guidance controller 130 will repeatedly show guided manipulation suggestions until it acquires enough views to stitch together a full view of view of the anatomical structure to commence with a partially or fully exposure of the hidden anatomical feature.

In practice of stages S120, S122 and S124, the visual guidance controller 130 first analyzes the present instantaneous endoscope view 11. If the visual guidance controller 130 does not have a complete understanding of what is in the endoscopic view 11 (i.e., an unknown view 111), then the visual guidance controller 130 generates guided manipulation anchor(s) and overlays the anchor(s) onto the endoscope view 11, so that the clinician knows where to perform the guided manipulation. The clinician may carry out the indicated guided manipulation, thus putting the anatomical structure AS in the view to a known or recognizable state. The state of knowing may be visual, tactile (through force sensing), or other measures engaged by the clinician in the act of manipulating the anatomical structure AS. The visual guidance controller 130, then analyzes and incorporates the new information revealed into knowledge base 40, which the visual guidance controller subsequently draws upon to guide the clinician later in the procedure.

An example of knowledge base 40 is a preoperative volume scan (e.g., a CT scan or a MRI can), which captures a state of the anatomical structure AS at a point of time before the procedure. The mapping between a preoperative volume scan and an endoscope image may not be fully known at the start of surgery for a variety of reasons. For example, the images are acquired using different modalities, so the images capture similar information in different ways, which have to be resolved. By further example, the state of the anatomical region AR changes between preoperative and intraoperative states via processes such as deformation or body position, which have to be resolved. Intraoperative view in the endoscope does not capture the full anatomical structure AS under consideration and may be ambiguous as to a relation to the preoperative volume scan, in which case more views must be acquired intraoperatively to match endoscopic images to the preoperative counterpart.

Knowledge base 40 may also be sourced from past data. The data may be a statistical compilation or learned using machine learning techniques. The data may include preoperative images, intraoperative images used in surgery, or even non-image data such as forces, task sequences, etc. In other words, information about a patient may be seeded by information sources that come from somewhere other than the patient, and as the surgery progresses the generic information may be tuned to better match the patient.

If the visual guidance controller starts with a partial mapping between a preoperative knowledge base 40 and endoscopic view 11, then the visual guidance controller may guide the clinician on how to manipulate known anatomical structure AS to expose those parts that yet unknown are unknown to the visual guidance controller. This may be of particular value if the clinician is looking for a part of the anatomical structure AS that is not currently in view. As an example, say neither the visual guidance controller nor the clinician knows where a major blood vessel is located within anatomical region AR, but based on a knowledge base 40 and current endoscopic view 11, the visual guidance controller may infer where the blood vessel may be in anatomical region AR. Then the visual guidance controller may guide the clinician on manipulations of the anatomical structure AS that may reveal the hidden vessel. Location markings and motion directives of guided manipulations of anatomical structure AS may be suggested by the visual guidance controller in order to reveal visual, tactile, and other forms of anatomical structure AS properties, depending on the sensing elements utilized by visual guidance controller.

This visual endoscopic guidance method preferably takes place with minimal disruption to the clinician's workflow, i.e., the clinician must be able to perform the procedure naturally without being distracted to respond to the visual guidance controller. The visual guidance controller also must be able to provide manipulation guidance judiciously by interpreting the state of the procedure or clinician needs.

Still referring to FIG. 9, in the previous embodiment, the visual guidance controller does not have complete understanding (e.g., a mapping from live endoscopy to preoperative knowledge base 40), but has enough understanding to guide the clinician on how to manipulate anatomical structure AS to gain a better mapping. In this embodiment, the visual guidance controller already recognizes what the visual guidance controller sees in the view (e.g., a known view 112), and may thus help guide the clinician on how to manipulate the anatomical structure AS in order for the clinician to partially or fully expose the hidden anatomical feature.

For example, as previously described for FIG. 3 herein, an endoscopic view 11d of a liver is at an oblique angle, which makes it difficult for the clinician to recognize the liver. This is represented by the oblique shaded square. The visual guidance controller understands that a critical vessel or tumor is in that location, and instructs the clinician on where and how to grasp the organ so that stretch the liver whereby the clinician may find see the critical vessel/tumor in an endoscopic view 11e. In this view, the liver is now at an upright facing angle view, making it easier and faster for a clinician to interpret and find clinically relevant features.

Alternatively, the visual guidance controller may see the liver at such an oblique angle in endoscopic view 11d of the liver that the visual guidance controller cannot precisely recognize the liver or register the liver to knowledge base 40. So the visual guidance controller may at least determine the angle that the liver needs to be facing to be more visually recognizable, so it computes a location on the liver for the clinician to grasp and a direction for the clinician to pull. When the clinician proceeds with this guidance, the result is a view that the visual guidance controller may recognize with high confidence. This in turn allows the visual guidance controller to fuse different information sources into the same view to help clinicians find things further.

In practice, the visual guidance controller may need to know a rough location of the anatomical structure AS within the anatomical region AR in order to suggest to the clinician how to manipulate the anatomical structure AS. For example, for endoscopic view 11 may be recognizable by the visual guidance controller but insufficient for 3D registration required for 3D overlays, the visual guidance controller may implement a base view classifier (e.g., a convolutional neural network) may be trained as known in the art of the present disclosure to communicate, such as, for example, "This 2D view requires manipulation of anatomical structure AS roughly at this mark and/or in this direction."

Still referring to FIG. 9, in another exemplary embodiment, the visual guidance controller may rely on a judgment of the clinician. More particularly, in a guided view 113 of stage S124, the visual guidance controller shows guide manipulation anchors 52 on a preoperative model 12 as previous described for FIG. 3 herein, and the clinician follows that guide in an endoscopic view 11, which has the effect of correlating the preoperative model 12 and endoscopic view 11. While a single such instance may be insufficient to generate a complete mapping or registration between the preoperative model 12 and endoscopic view 11, multiple, carefully planned instances may generate enough corresponding information. Alternatively, a preoperative image be whereby the clinician looks at a raw view of the endoscopic view 11, uses clinical judgement to find the corresponding anchor(s) on the anatomical structure, and then manipulates those anchor(s) to register the endoscopic view 11 to the preoperative image.

Still referring to FIG. 9, during an initial phase 123a of stage S122, the visual guidance controller generates guided manipulation anchor(s) for guiding manipulation of anatomical structure AS by examining the anatomical structure AS and correlating it to a knowledge base 40. The assumption is that there is an overlap of information, but the connection between endoscopic view 11 and the knowledge base 40 may be incomplete. The visual guidance controller then uses what it knows to guide the clinician to reveal what it does not know, to improve its knowledge base 40. In this case, the visual guidance controller has partial information.

In the case where the visual guidance controller has full information in one modality (e.g., endoscopy and preoperative images), then the visual guidance controller may use that knowledge to generate guided manipulation anchor(s) for anatomical structure AS manipulation guidance in order to gain further data of a different modality (e.g., force).

As previously described in the present disclosure, knowledge base 40 may have numerous and various sources of information that may be used to generate a new set of guided manipulation anchor(s). Examples of these sources includes, but are not limited to, preoperative and intraoperative images, information on anatomical structure non-image in nature, statistical compilations of images from past procedures, and knowledge that is learned from past procedures.

The guided manipulation anchors may also be seeded by the clinician using an interactive virtual marking system. In this embodiment, the visual guidance controller does not have complete information about the anatomical region, but it may have some loosely coupled preoperative information. The clinician may then use an instrument to label some features they see on the anatomical structure AS, and the virtual labels may be incorporated into the knowledge base 40, allowing the visual guidance controller to provide image and manipulation guidance later on in the surgery.

For example, the visual guidance controller may incorporate interactive labeling system as known in the art of the present disclosure or hereinafter conceived whereby the clinician uses an instrument to virtually mark and label the anatomical structure AS in the endoscopic view 11 (e.g., a marking via stars indicating locations of a tumor margin, an airway and a vessel). The visual guidance controller may then combine this knowledge in real time with its existing knowledge base 40 to provide further anatomical structure manipulation guidance.

In practice, the visual guidance controller may generate guided manipulation anchors for the clinician without having semantic information as well. In an embodiment, the visual guidance controller detects salient image patterns of interest. Examples of salient patterns include, but are not limited to, high texture areas, areas of common texture or appearance, areas of high contrast compared to its neighbors, patterns that have not been seen before, patterns that have been seen before, patterns that have been seen repeatedly, areas adjacent to areas that are semantically identifiable, and so on. More particularly, the trackable patterns in the anatomical structure AS may be found using a well-known algorithm (e.g., SURF) and the visual guidance controller finds a persistent label for these areas. These labels may be refined further to decide on which are to become guided manipulation anchors, as mentioned above.

Still referring to FIG. 9, in one embodiment of stage S124, an initial phase S125a involves the visual guidance controller finding hidden anatomical feature HF that the controller is able to identify with a low degree of confidence. This sets the seed for the visual guidance controller to follow up on those hidden anatomical feature HP by instructing the clinician to manipulate the anatomical structure during a phase 123b of stage S122 in such a way that new sets of appearances of the anatomical structure during a phase 125b of stage S124 either confirms or eliminates the initial crude identification(s) of a position of a hidden anatomical feature HAF within the anatomical structure AS.

More particularly, after the clinician performs the initial guided manipulation of the anatomical structure during phase 123a of stage S122, the visual guidance controller may select a course of action to take depending on circumstances and preferences. For example, the visual guidance controller may show a hidden feature anchor with a degree of fidelity that matches the confidence in the recognition of the view of the anatomical structure. In this scenario the visual guidance controller has recognized the present view of the anatomical structure from past data, be it from past procedures, past views of the current procedure, models, surgeon labeling or some hybrid thereof. This cycle can be iterative as confidence on tissue in question increases, hidden feature anchor can be more complete and more elaborate. Alternatively, if the visual guidance controller has confidence in the correlation that is below a threshold, or if an anatomical feature of interest is still hidden within the field of view, the visual guidance controller can suggest further guided manipulation.

Still referring to FIG. 9, the practice of stages S120, S122 and S124 is an endoscopic procedure includes an initial planning phase involving a pre-operative or an intra-operative volume scan of anatomical structure AS within anatomical region AR. From the volume scan, the clinician utilizes endoscopic viewing controller 20 or other controller as known in the art of the present disclosure to identify one or more target view(s) within the volume scan of anatomical structure AS for performing a diagnosis, a treatment or a surgery. Depending on the state of the anatomical structure and the goal of the endoscopic procedure, an entirety of the target view may or may not be viewable by an endoscope 10 when endoscope 10 is positioned within a patient.

More particularly, a planning interface as known in the art of the present disclosure may be used for viewing and annotating 2D and 3D data for the purpose of ascertaining target view(s) of the anatomical structure during the procedure. This may be done intra-operatively in the endoscope view involving a fusion of an endoscopic image and volume image, because such an endoscope plan may be done on volumetric image of patient anatomy considering geometries of anatomy and kinematics of the endoscope and other constraints in the clinician preferences. For example, a trocar position relative to the target organ (between the ribs) and geometry and motions of the endoscope (for straight endoscopes it will be the set of positions govern by rotation about the trocar entry point).

The planning phase further involves updating knowledge base 40 of visual guidance controller 130 with volume scan of the anatomical structure AS, a planned path, salient feature(s) of the anatomical structure and a task sequence whereby, prior to or concurrently with endoscope 10 being navigated within the anatomical region visual guide controller 130 may (1) ascertain a degree to which a target view will be visible to endoscope 10 and/or (2) ascertain one or more recognizable poses of a target view.

After the planning phase, the endoscopic procedure includes a navigation phase of endoscope 10 within the patient P whereby visual guidance controller 130 is correlating, to a highest degree possible, the endoscopic view of the anatomical region as the endoscope 10 is being navigated to a position relative to a target view.

One correlation embodiment encompasses visual guidance controller 130 attempting to ascertain, to a highest degree possible, the endoscopic view matching the target view within the volume scan stored within the knowledge base 40 as the endoscope 10 is being navigated to a position relative to a target view. Once positioned, if visual guidance controller 130 recognizes the endoscopic view matching the target view within the volume scan stored within the knowledge base 40, then visual guidance controller 130 will either generate guided manipulation anchors to expose invisible aspects of the anatomical structure or generate guided manipulation anchors to adjust a view of visible aspects of the anatomical structure.

Alternatively, a model of the anatomical structure or a compilation of images may be used in lieu of the volume scan.

Another correlation embodiment encompasses an attempted tracking, to the highest degree possible, of the endoscope navigated to a position relative to a target view. Once visual guidance controller 130 determines the endoscope reaches such a position per the planned path or tasks sequence in the knowledge base, if visual guidance controller 130 recognizes the endoscopic view matching the target view within the volume scan stored within the knowledge base 40, then visual guidance controller 130 will either then visual guidance controller 130 will either generate guided manipulation anchors to expose invisible aspects of the anatomical structure or generate guided manipulation anchors to adjust a view of visible aspects of the anatomical structure.

Again, alternatively, a model of the anatomical structure or a compilation of images may be used in lieu of the volume scan.

Another correlation embodiment encompasses an attempted identification, to the highest degree possible, of salient features of the anatomical structure adjacent the target view. Once visual guidance controller 130 determines the endoscope reaches such a position per the planned path or tasks sequence in the knowledge base, if visual guidance controller 130 recognizes the endoscopic view showing the salient features of the anatomical structure adjacent the target view within the volume scan stored within the knowledge base 40, then visual guidance controller 130 will either then visual guidance controller 130 will either generate guided manipulation anchors to expose invisible aspects of the anatomical structure or generate guided manipulation anchors to adjust a view of visible aspects of the anatomical structure.

Again, alternatively, a model of the anatomical structure or a compilation of images may be used in lieu of the volume scan.

Figure 10:
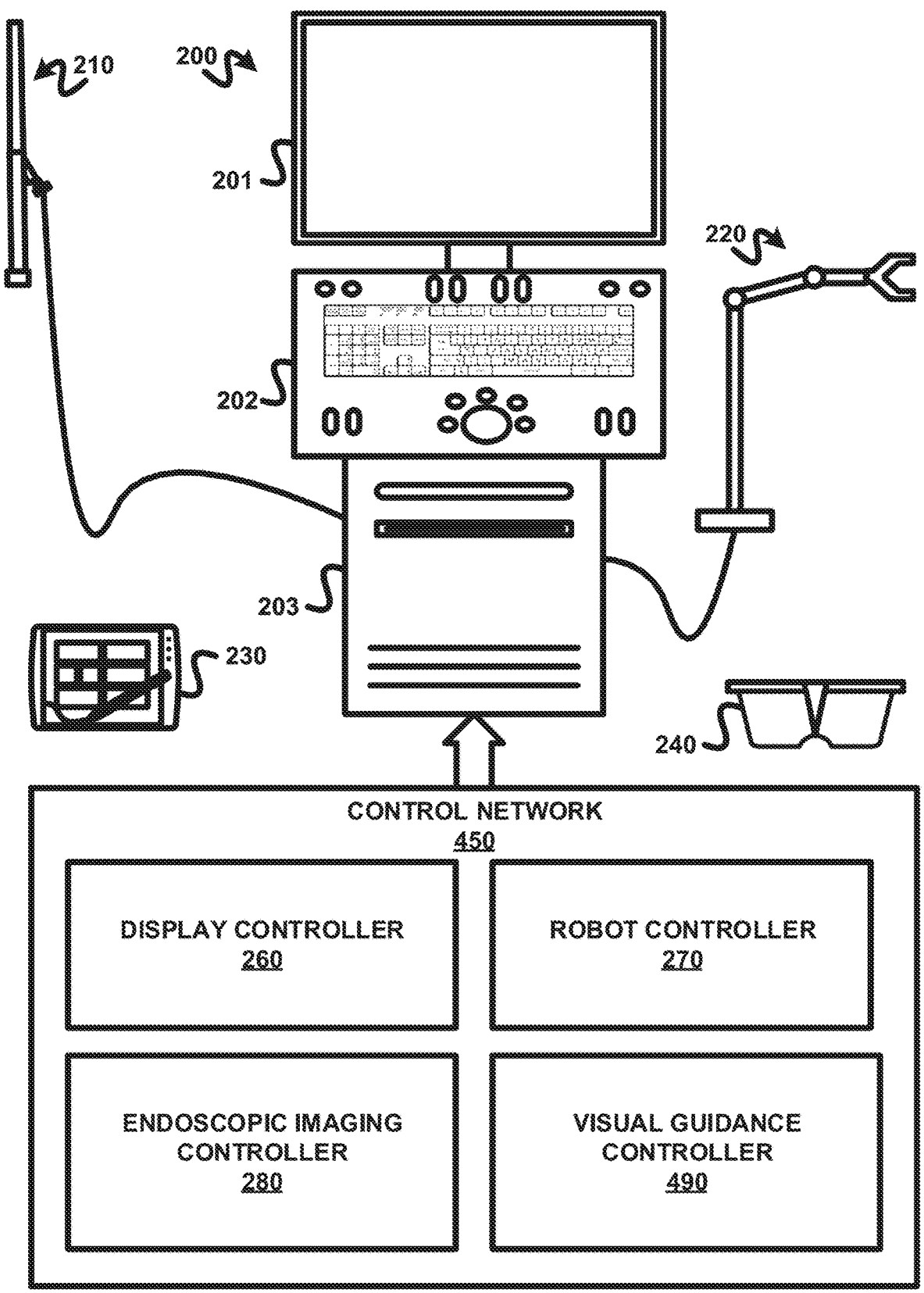
FIG. 10 illustrates an exemplary embodiment of a visual endoscopic guidance system in accordance with the present disclosure incorporating the visual endoscopic guidance device of FIG. 7.
Figure 11:
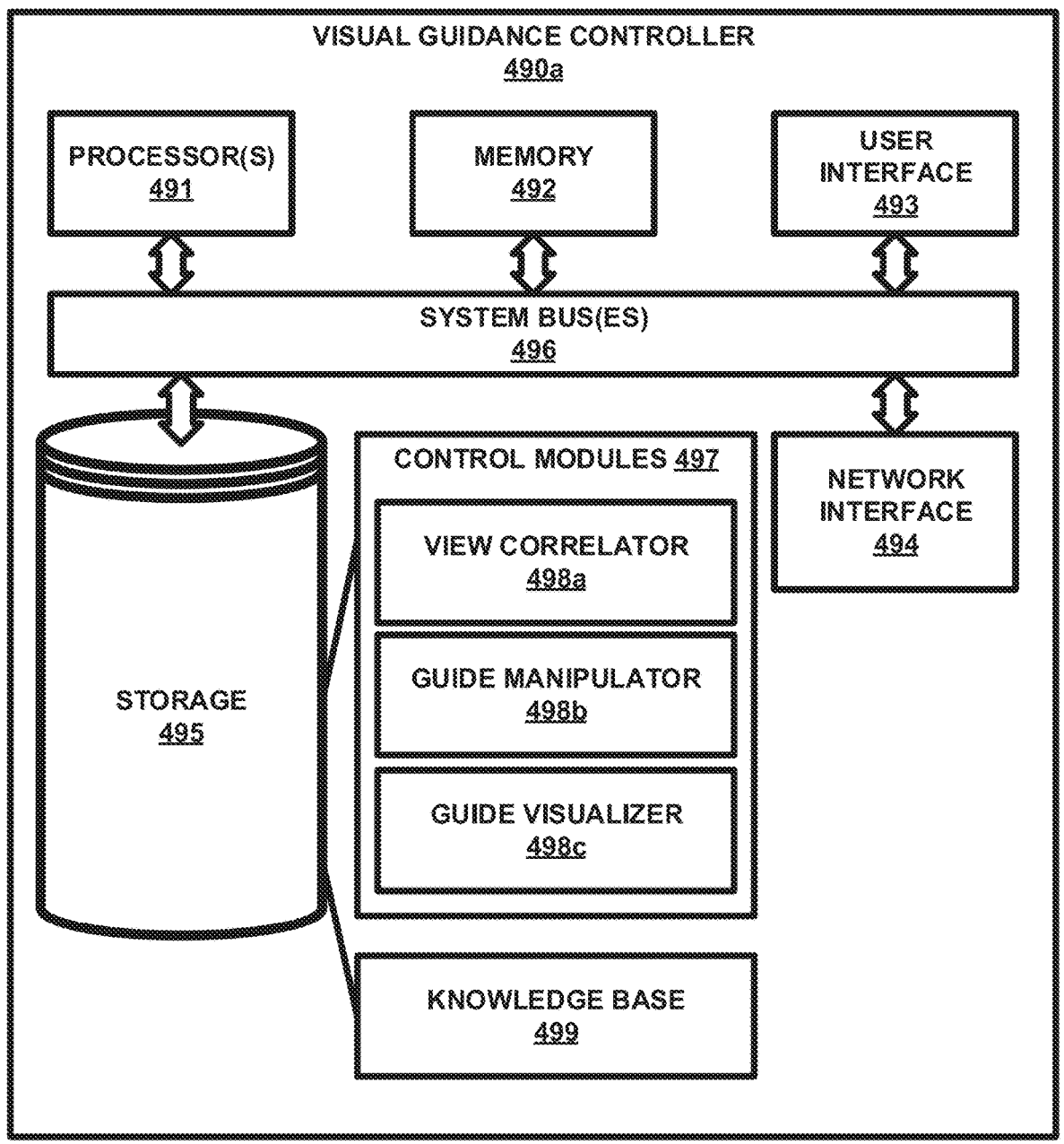
FIG. 11 illustrates an exemplary embodiment of a visual guidance controller in accordance with the present disclosure.

To facilitate a further understanding of the various inventions of the present disclosure, the following description of FIGS. 10 and 11 respectively teaches exemplary embodiments of a visual endoscopic guide system and a visual guidance controller of the present disclosure. From this description, those having ordinary skill in the art will appreciate how to apply various aspects of the present disclosure for making and using additional embodiments of visual endoscopic guide devices and visual guidance controllers of the present disclosure.

Referring to FIG. 10, in one exemplary embodiment, a visual endoscopic guide system of the present disclosure includes workstation 200 employing monitor 201, keyboard 202 and a computer 203. An endoscope 210 is in communication, wired or wireless, with workstation 200 as known in the art of the present disclosure or hereinafter received. An optional robot 220 for performing guided manipulations may also be communication, wired or wireless, with workstation 200.

A control network 450 of a display controller 260 as known in the art of the present disclosure or hereinafter conceived, a robot controller 270 as known in the art of the present disclosure or hereinafter conceived, an endoscopic imaging controller 280 as previously described in the present disclosure and a visual guidance controller 490 as previously described in the present disclosure are installed in workstation 200. Additional control networks 450 may be also be installed in a server (not shown), a mobile device (e.g., a tablet 230 as shown) and an augmented reality device (e.g., a head mounted display 240 as shown).

Still referring to FIG. 10, in practice, the specific mechanism involved to effect guided manipulation may serve as a basis on a determination on how the guidance is communicated to the clinician. For example, manual or robotic instruments (e.g., robot 220) may be used in an equivalent manner to grasp tissue based on guidance.

More particularly, the motion may assisted such that it is semi-automatic. For example with robotic tools, the clinician only needs to bring an end effector to the general region of the guided manipulative anchor, and then the robot can automatically perform the remainder of the grasp and manipulation as known in the art of the present disclosure.

In one exemplary embodiment, magnetic devices as known in the art of the present disclosure or hereinafter conceived may be used to effect guided manipulation. For example, Levita® Magnetics commercially provides a magnetic surgical platform including a magnetic module that sits on top of the patient's abdomen and a ferromagnetic module clip attached to the portion of the tissue to be pulled. This clip is inserted through surgical ports and deployed by clamping to the tissue to be held. The magnetic module is then placed on top of the patient's abdomen, attracting the ferromagnetic module towards the magnetic module the process, thereby holding the tissue suspended to expose other tissue.

In practice, where there are multiple methods to grasp and move anatomical structure(s) (e.g., tissue), guided manipulation anchors may be shown in a way that distinguishes which type of method(s) should be used for a given grasp instance. This is also a way visual guidance controller 490 may predict a result of the grasp maneuver, based on the grasping mechanism used. Visual guidance controller 490 further remind the clinician that detachable clips are in place, and may instruct the clinician on how to move the magnetic module to achieve a grasp maneuver.

Referring to FIG. 11, a visual guidance controller 490a is an exemplary embodiment of visual guidance controller 490 (FIG. 10) including one or more processor(s) 491, memory 492, a user interface 493, a network interface 494, and a storage 495 interconnected via one or more system buses 496.

Each processor 491 may be any hardware device, as known in the art of the present disclosure or hereinafter conceived, capable of executing instructions stored in memory 492 or storage or otherwise processing data. In a non-limiting example, the processor(s) 491 may include a microprocessor, field programmable gate array (FPGA), application-specific integrated circuit (ASIC), or other similar devices.

The memory 492 may include various memories, as known in the art of the present disclosure or hereinafter conceived, including, but not limited to, L1, L2, or L3 cache or system memory. In a non-limiting example, the memory 492 may include static random access memory (SRAM), dynamic RAM (DRAM), flash memory, read only memory (ROM), or other similar memory devices.

The user interface 493 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 494.

The network interface 494 may include one or more devices, as known in the art of the present disclosure or hereinafter conceived, for enabling communication with other hardware devices. In a non-limiting example, the network interface 494 may include a network interface card (NIC) configured to communicate according to the Ethernet protocol. Additionally, the network interface 494 may implement a TCP/IP stack for communication according to the TCP/IP protocols. Various alternative or additional hardware or configurations for the network interface 494 will be apparent.

The storage 495 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 495 may store instructions for execution by the processor(s) 491 or data upon with the processor(s) 491 may operate. For example, the storage 495 may store a base operating system for controlling various basic operations of the hardware.

The storage 495 also stores application modules in the form of executable software/firmware for implementing the various functions of the visual guidance controller 490a as previously described in the present disclosure including, but not limited to, a view correlator 498a, a guide manipulator 498b and an guide visualizer 498c. Storage S295 also stores a knowledge base 499 in accordance with the various embodiments of knowledge bases as previously described in the present disclosure.

Figure 12:
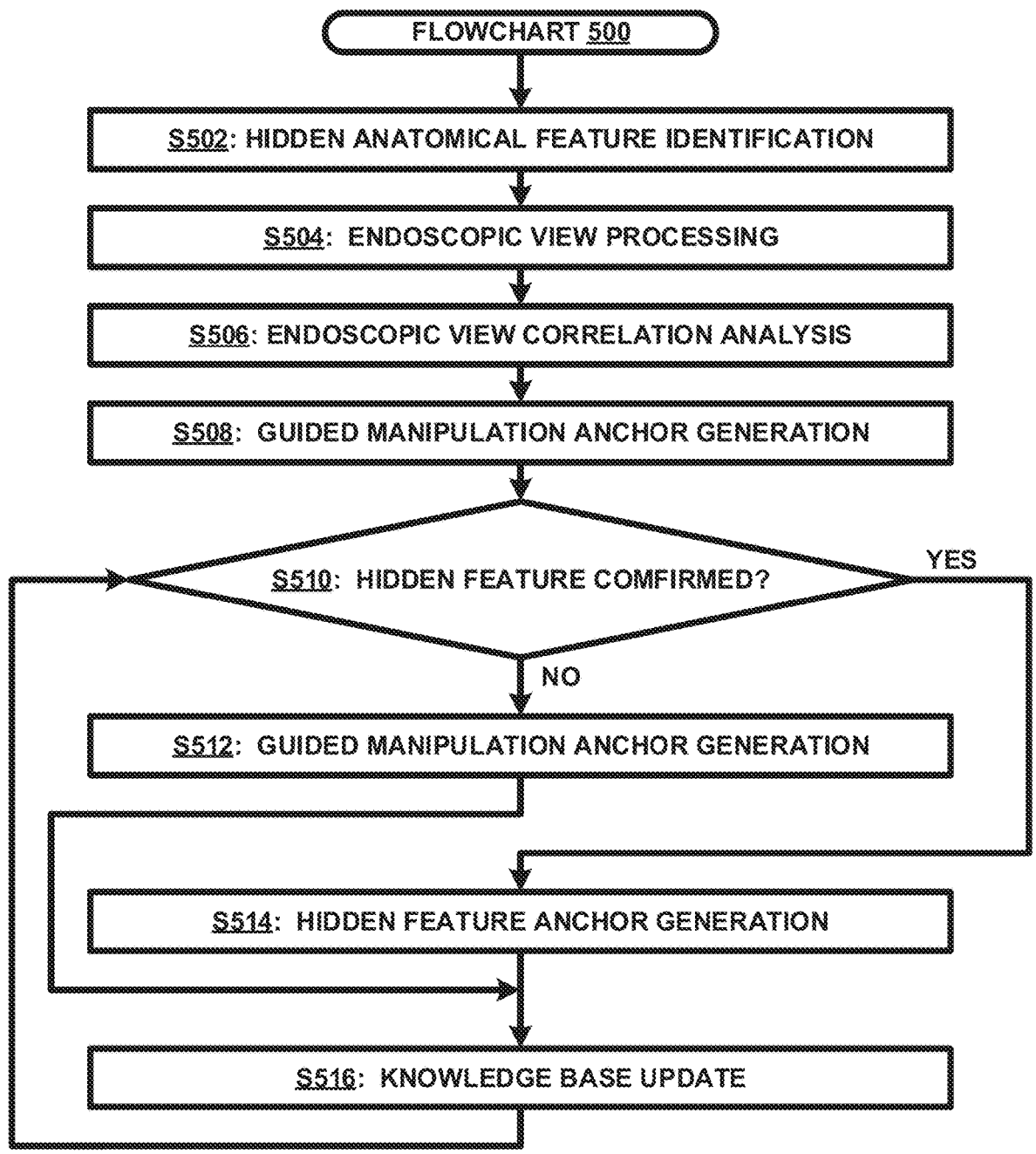
FIG. 12 illustrates a flowchart representative of an exemplary embodiment of a visual guidance method in accordance with the present disclosure executable by the visual guidance controller of FIG. 4.

FIG. 12 illustrate a flowchart 300 representative of a visual guidance method of the present discloses executable by view correlator 498a, guide manipulator 498b and guide visualizer 498c of FIG. 12.

Referring to FIG. 12, a stage S502 of flowchart 500 involves view correlator 498a finding a hidden anatomical interest within an anatomical structure whereby view correlator 498a has a low confidence (e.g., ≤20%) chance that view correlator 498a has delineated a correct position of the hidden anatomical interest within the anatomical structure.

A stage S504 of flowchart 500 involves view correlator 498a receiving or identifying an endoscopic view of an anatomical structure as previously described in the present disclosure, and a stage S506 of flowchart 500 involves view correlator 498a performing a correlation analysis of an endoscopic view of an anatomical structure as previously described in the present disclosure. More particularly, view correlator 498a relates, to the best degree possible, the endoscope view to a knowledge base of images(s), model(s) and/or procedure detail(s) of the endoscopic procedure. For example, view correlator 498 determines, to the best degree possible, a position of endoscopic view of an anatomical structure within a volume scan of an anatomical region or on an anatomical model via registration techniques as known in the art of the present disclosure or from a tracking of the endoscope indicative of a camera positioning of the endoscope relative to the anatomical region.

Still referring to FIG. 12, a stage S508 of flowchart 500 involves guide manipulator 498b generating initial guided manipulation anchors as needed to manipulate the anatomical structure into a recognized state.

During a stage S510 of flowchart 500, view correlator 498a reiterates stages S504 and S506 to determine if the clinician manipulated the anatomical structure as guided by the guided manipulation anchors of stage S508 whereby the position of the hidden anatomical feature within the anatomical structure can be confirmed.

If the position of the hidden anatomical feature within the anatomical structure can be confirmed during stage S510, then guide visualizer 498 proceeds to a stage S514 of flowchart 500 to generate a hidden feature anchor with a degree of fidelity that matches the confidence by view correlator 498a in the recognition of the endoscopic view and then proceeds to a stage S516 of flowchart 500 to augments an internal, personalized model of the anatomical structure within the knowledge base with information gleaned from the visualization, manipulation, and interaction processes. The model starts as a generic statistical compilation, and then becomes tuned to the patient as more patient-specific information is revealed.

In one embodiment of stage S510, view correlator 498a may confirm the position of hidden anatomical feature within the anatomical structure in the present endoscopic view from previous endoscopic view(s), previous endoscopic procedure(s), anatomical model(s), surgeon labeling or some hybrid thereof. A cycle of stage S510, S514 and S5165 may be iterative as shown whereby as confidence in the position of the hidden anatomical feature increases, the hidden feature anchor may become complete and more elaborate.

Figure 13:
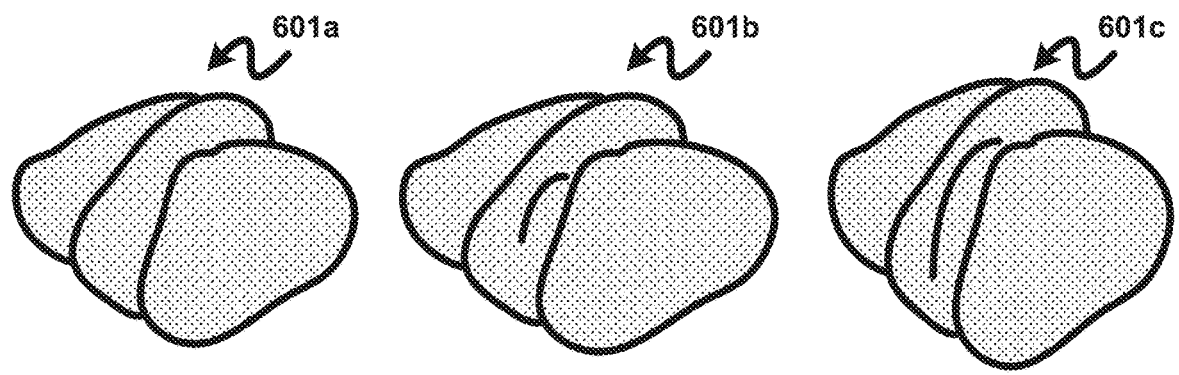
FIG. 13 illustrates an exemplary generation of a hidden feature anchor in accordance with the present disclosure.

For example, FIG. 13 illustrates an initial endoscopic view 601a of a lung whereby as the lung is stretched in accordance with guided manipulation anchors, a size of a hidden feature anchor (shown as an arc) representative of a major airway in the lung is expanding over a second endoscopic view 601b and a third endoscopic view 601c to more clearly expose the position of the major airway in the lung.

If view correlator 498a is unable to may confirm the position of hidden anatomical feature within the anatomical structure in the present endoscopic view in view of a confidence by the view correlator 498a in the present endoscopic view is below a threshold, or if an anatomical feature of interest remains completely hidden within the field of view of the present endoscopic view, then guide manipulator 498b proceeds to a stage S512 to generate additional guided manipulation anchor(s) as needed to manipulate the anatomical structure into a more recognizable state that will reveal the hidden anatomical feature and then proceeds to stage S516 to update the knowledge base as previously described.

Flowchart 500 is continually repeated as the procedures progresses, providing a real-time interactive guidance to the clinicians as the clinician explores tissue and perform tasks.

Still referring to FIG. 12, in practice, the decision by view correlator 498a during stage S510 n to either display an hidden feature anchor during stage S514 or to display additional guided manipulation anchors during stage S512 may be based on the following criteria including, but not limited to, (1) a confidence in recognition of the endoscopic view, (2) relationships of unknown image areas to known image features, (3) criticality of the information the clinician needs at given times in the procedure, and (4) spatial relationships between overlapping anatomical features. For the latter case, if anatomical features A and B are overlapping in the endoscopic view, the view correlator 498a may show anatomical feature A if anatomical feature A is on top, or ask the clinician to move anatomical feature A in order to reveal anatomical feature B, depending on whether anatomical feature B is important to be seen at that time.

In an alternative embodiment, view correlator 598a may use a hybrid approach between stages S512 and S514 when confidence in the image detection of the anatomical features is present but imperfect. For example, view correlator 598a may indicate the anatomical feature using text or other symbolic icons rather than a hidden feature anchor, which would indicate precise positions or orientations. This at least provides clinicians with information about image content, and in parallel, guide manipulator 498b may prompt the clinician to perform manipulations via additional guided manipulations anchors that may help view correlator 498a to complete the picture or confirm the hypotheses.

Still referring to FIG. 12, while the many variants of endoscopic procedure may have their own unique difficulties, a common challenge that is pervasive over many procedures includes the limited endoscopic field of view, as compared to what clinicians are used to under traditional direct vision. This means clinicians must cognitively stitch together views previously seen into a coherent mental map, which is made difficult by the real-time cognitive demands of the procedure combined with appearances of anatomical structure(s) that are not immediately recognizable.

Figure 14:
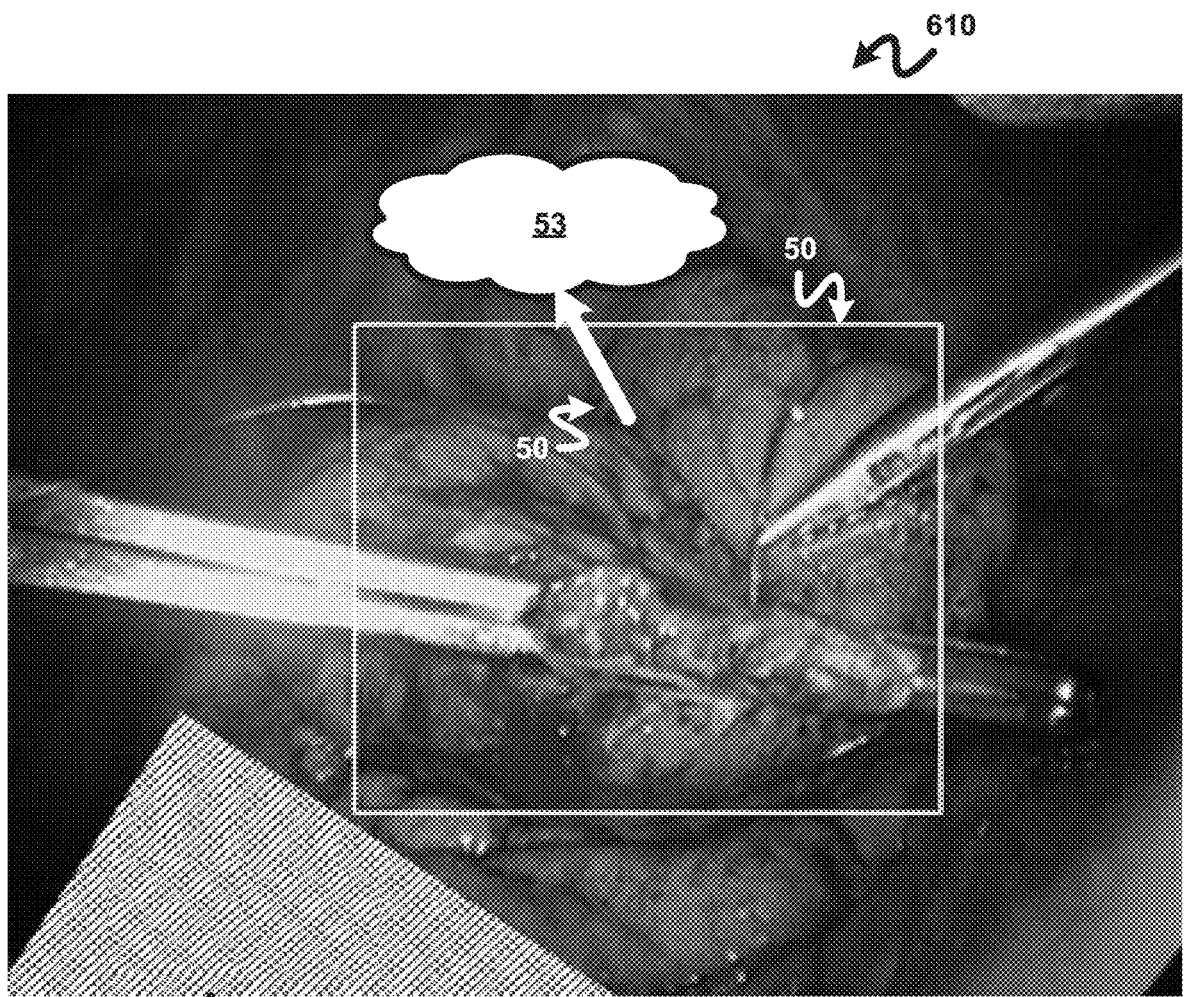
FIG. 14 illustrates an exemplary image map in accordance with the present disclosure.

A feature of the visual manipulation controller of the current disclosure is the ability to stitch together a large field of view of an image map 610 based on past and current images as shown in FIG. 14. One image-stitching technique involves a finding anatomical features that are outside of the field of endoscopic view (e.g., tumor 153), and a black arrow pointing from the live endoscopic image clinicians into the past data of the image map 610. The live endoscopic view may be indicated by a full color image area, while the past endoscopic views may be stitched together are indicated by the black and white regions.

A second image-stitching technique is manipulation guidance to provide the controller with more data pertaining to incomplete information. This is shown in FIG. 14 as area 203 and the option for the clinician is to follow that guidance so that the controller may fill in the blanked out area 203 whereby more information may be fused based on statistical data or explicit recognition.

The past portions of the stitched image map can be shaded based on how stale the images are as well, and in turn can be used to generate manipulation guidance for the clinicians to refresh stale map areas; extents to which those suggestions are imposed may be computed as a function of the criticality of those regions. If the stale regions are known to be of little import, the controller may elect to recommend against refreshing it, to make the procedure more efficient overall.

Referring to FIGS. 1-14, those having ordinary skill in the art of the present disclosure will appreciate numerous benefits of the present disclosure including, but not limited to guidance suggestions for a clinician (e.g., a radiologist, a therapist or a surgeon) on how to manually or robotically manipulate anatomical structure(s) (e.g., tissue, bone, nerves and blood vessels) in an endoscopic view that may (1) reveal hidden features of anatomical structure(s) within the endoscopic view and (2) position and/or orient tissue to facilitate an analysis of the anatomical structure(s) within the endoscopic view.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

The terms "signal", "data" and "command" as used in the present disclosure broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication between various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A visual endoscopic guidance device comprising:
an endoscopic viewing controller configured to control a display of an endoscopic view of an anatomical structure; and
a visual guidance controller configured to:
   determine a motion direction to apply motion to expose a hidden feature of the anatomical structure, wherein the motion direction is determined based on position of the hidden feature of the anatomical structure relative to the endoscopic view of the anatomical structure,
   control a display of a guided manipulation anchor within the display of the endoscopic view of the anatomical structure, the guided manipulation anchor comprising a visual indicator configured to guide manipulation of the anatomical structure to expose the hidden feature of the anatomical structure, wherein the visual indicator indicates the motion direction to apply motion to expose the hidden feature of the anatomical structure, and
   control a display of a hidden feature anchor relative to the display of the endoscopic view of the anatomical structure, the hidden feature anchor representative of position of a guided visualization of the hidden feature of the anatomical structure.

2. The visual endoscopic guidance device of claim 1, wherein the visual guidance controller is further configured to:
control the display of the hidden feature anchor within the display of the endoscopic view of the anatomical structure.

3. The visual endoscopic guidance device of claim 1, wherein the visual guidance controller is further configured to:
control the display of the hidden feature anchor within a display of an image map including the endoscopic view of the anatomical structure.

4. The visual endoscopic guidance device of claim 1, wherein the visual guidance controller is further configured to:
ascertain a degree of identification of a position of the hidden feature of the anatomical structure relative to the display of the endoscopic view of the anatomical structure; and
derive the guided manipulation anchor based on the degree of identification of the position of the hidden feature of the anatomical structure relative to the display of the endoscopic view of the anatomical structure.

5. The visual endoscopic guidance device of claim 1, wherein the visual guidance controller is further configured to:
ascertain a degree of identification of a position of the hidden feature of the anatomical structure relative to the display of the endoscopic view of the anatomical structure; and
derive the hidden feature anchor based on the degree of identification of the position of the hidden feature of the anatomical structure relative to the display of the endoscopic view of the anatomical structure.

6. A visual guidance controller comprising:
a processor communicatively coupled to memory, the processor configured to:
   determine a motion direction to apply motion to expose a hidden feature of the anatomical structure, wherein the motion direction is determined based on position of the hidden feature of the anatomical structure relative to the endoscopic view of the anatomical structure;
   control a display of a guided manipulation anchor within a display of an endoscopic view of an anatomical structure, the guided manipulation anchor comprising a visual indicator configured to guide manipulation of the anatomical structure to expose the hidden feature of the anatomical structure, wherein the visual indicator indicates the motion direction to apply motion to expose the hidden feature of the anatomical structure; and
   control a display of a hidden feature anchor relative to the display of the endoscopic view of the anatomical structure, the hidden feature anchor representative of a position of a guided visualization of the hidden feature of the anatomical structure.

7. The visual guidance controller of claim 6, wherein the processor is further configured to:
control the display of the hidden feature anchor within the display of the endoscopic view of the anatomical structure.

8. The visual guidance controller of claim 6, wherein the processor is further configured to:
control the display of the hidden feature anchor within a display of an image map including the endoscopic view of the anatomical structure.

9. The visual guidance controller of claim 6, wherein the processor is further configured to:
ascertain a degree of identification of a position of the hidden feature of the anatomical structure relative to the display of the endoscopic view of the anatomical structure; and
derive the guided manipulation anchor based on the degree of identification of the position of the hidden feature of the anatomical structure relative to the display of the endoscopic view of the anatomical structure.

10. The visual guidance controller of claim 6, wherein the processor is further configured to:
   ascertain a degree of identification of a position of the hidden feature of the anatomical structure relative to the display of the endoscopic view of the anatomical structure; and
   derive the hidden feature anchor based on the degree of identification of the position of the hidden feature of the anatomical structure relative to the display of the endoscopic view of the anatomical structure.

11. A visual endoscopic guidance method comprising:
   determining a motion direction to apply motion to expose a hidden feature of the anatomical structure, wherein the motion direction is determined based on position of the hidden feature of the anatomical structure relative to the endoscopic view of the anatomical structure;
   controlling, by a visual guidance controller, a display of a guided manipulation anchor within a display of an endoscopic view of an anatomical structure, the guided manipulation anchor comprising a visual indicator configured to guide manipulation of the anatomical structure to expose the hidden feature of the anatomical structure, wherein the visual indicator the motion direction to apply motion to expose the hidden feature of the anatomical structure; and
   controlling, by the visual guidance controller, display of a hidden feature anchor relative to the display of the endoscopic view of the anatomical structure, the hidden feature anchor representative of position of a guided visualization of the hidden feature of the anatomical structure.

12. The visual endoscopic guidance method of claim 11, further comprising:
   controlling, by the visual guidance controller, the display of the hidden feature anchor within the display of the endoscopic view of the anatomical structure.

13. The visual endoscopic guidance method of claim 11, further comprising:
   controlling, by the visual guidance controller, the display of the hidden feature anchor within a display of an image map including the endoscopic view of the anatomical structure.

14. The visual endoscopic guidance method of claim 11, further comprising:
   ascertaining, by the visual guidance controller, a degree of identification of a position of the hidden feature of the anatomical structure relative to the display of the endoscopic view of the anatomical structure; and
   deriving, by the visual guidance controller, the guided manipulation anchor based on the degree of identification of the position of the hidden feature of the anatomical structure relative to the display of the endoscopic view of the anatomical structure.

15. The visual endoscopic guidance method of claim 11, further comprising:
   ascertaining, by the visual guidance controller, a degree of identification of a position of the hidden feature of the anatomical structure relative to the display of the endoscopic view of the anatomical structure; and
   deriving, by the visual guidance controller, the hidden feature anchor based on the degree of identification of the position of the hidden feature of the anatomical structure relative to the display of the endoscopic view of the anatomical structure.

16. The visual endoscopic guidance device of claim 1, wherein the visual indicator of the guided manipulation anchor further includes a location marking that indicates a location associated with the anatomical structure to manipulate to expose the hidden feature of the anatomical structure.

17. The visual guidance controller of claim 6, wherein the visual indicator of the guided manipulation anchor further includes a location marking that indicates a location associated with the anatomical structure to manipulate to expose the hidden feature of the anatomical structure.

18. The visual endoscopic guidance method of claim 11, wherein the visual indicator of the guided manipulation anchor further includes a location marking indicating a location associated with the anatomical structure to manipulate to expose the hidden feature of the anatomical structure.

* * * * *